(12) United States Patent
Fevola et al.

(10) Patent No.: US 10,159,638 B2
(45) Date of Patent: Dec. 25, 2018

(54) PERSONAL CARE COMPOSITIONS CONTAINING COMPLEXING POLYELECTROLYTES

(71) Applicant: Johnson & Johnson Consumer Inc., Skillman, NJ (US)

(72) Inventors: Michael J. Fevola, Belle Mead, NJ (US); Tobias J. Fuetterer, Princeton, NJ (US); Matthew A. Lohr, Ewing, NJ (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 14 days.

(21) Appl. No.: 15/278,184

(22) Filed: Sep. 28, 2016

(65) Prior Publication Data

US 2017/0360688 A1  Dec. 21, 2017

Related U.S. Application Data

(60) Provisional application No. 62/352,713, filed on Jun. 21, 2016.

(51) Int. Cl.
| | | |
|---|---|---|
| *A61K 8/44* | (2006.01) | |
| *A61K 8/46* | (2006.01) | |
| *A61K 8/73* | (2006.01) | |
| *A61Q 19/10* | (2006.01) | |
| *A61K 8/81* | (2006.01) | |
| *A61K 8/368* | (2006.01) | |
| *A61Q 5/02* | (2006.01) | |
| *A61Q 5/12* | (2006.01) | |

(52) U.S. Cl.
CPC ............ *A61K 8/8182* (2013.01); *A61K 8/368* (2013.01); *A61K 8/442* (2013.01); *A61K 8/463* (2013.01); *A61K 8/73* (2013.01); *A61K 8/731* (2013.01); *A61K 8/737* (2013.01); *A61K 8/817* (2013.01); *A61K 8/8147* (2013.01); *A61K 8/8152* (2013.01); *A61K 8/8188* (2013.01); *A61Q 5/02* (2013.01); *A61Q 5/12* (2013.01); *A61Q 19/10* (2013.01); *A61K 2800/49* (2013.01); *A61K 2800/5422* (2013.01); *A61K 2800/5424* (2013.01); *A61K 2800/5426* (2013.01); *A61K 2800/5428* (2013.01); *A61K 2800/594* (2013.01)

(58) Field of Classification Search
CPC ....... A61K 8/8182; A61K 8/368; A61K 8/442
See application file for complete search history.

(56) References Cited

U.S. PATENT DOCUMENTS

| | | |
|---|---|---|
| 3,035,004 A | 5/1962 | Glavis |
| 3,958,581 A | 5/1976 | Abegg et al. |
| 3,962,418 A | 6/1976 | Birkofer |
| 4,240,450 A | 12/1980 | Cauwet et al. |
| 4,299,817 A | 11/1981 | Hannan, III et al. |
| 5,292,843 A | 3/1994 | Jenkins et al. |
| 5,858,938 A | 1/1999 | Glenn, Jr. et al. |
| 5,876,705 A | 3/1999 | Uchiyama et al. |
| 6,106,815 A * | 8/2000 | Kang ...................... A61K 8/11 424/451 |
| 6,897,253 B2 | 5/2005 | Schmucker Castner et al. |
| 7,288,616 B2 | 10/2007 | Tamareselvy et al. |
| 7,335,627 B1 | 2/2008 | O'Lenick et al. |
| 7,375,064 B1 | 5/2008 | O'Lenick, Jr. |
| 7,507,399 B1 | 3/2009 | O'Lenick, Jr. |
| 7,776,318 B2 | 8/2010 | Bissey-Beugras et al. |
| 7,998,222 B2 | 8/2011 | Morrissey et al. |
| 8,883,700 B2 | 11/2014 | Perez-Prat Vineusa et al. |
| 8,980,239 B2 | 3/2015 | Staudigel et al. |
| 9,090,727 B2 | 7/2015 | Hough et al. |
| 9,096,755 B2 | 8/2015 | Chari et al. |
| 9,101,551 B2 | 8/2015 | Stella et al. |
| 9,162,085 B2 | 10/2015 | Dihora et al. |
| 9,187,590 B2 | 11/2015 | Tamareselvy et al. |
| 9,265,975 B2 | 2/2016 | Counradi et al. |
| 2003/0108507 A1 | 6/2003 | Clipson et al. |
| 2004/0234483 A1 | 11/2004 | Peffly et al. |
| 2006/0018857 A1 | 1/2006 | Behler et al. |
| 2006/0251603 A1 * | 11/2006 | Rigoletto, Jr. .......... A61K 8/731 424/70.13 |
| 2006/0270563 A1 | 11/2006 | Yang et al. |
| 2006/0293197 A1 | 12/2006 | Uehara et al. |
| 2012/0244200 A1 | 9/2012 | Haskel et al. |
| 2016/0106647 A1 | 4/2016 | Fevola et al. |
| 2016/0167040 A1 | 6/2016 | Braun et al. |
| 2017/0007526 A1 | 1/2017 | Horie et al. |

FOREIGN PATENT DOCUMENTS

| | | |
|---|---|---|
| WO | WO 2003/032935 A | 4/2003 |
| WO | WO 2004/064802 A | 8/2004 |

(Continued)

OTHER PUBLICATIONS

Fevola, M., Exerpts from "Profile of Polyquaternium-6", Cosmetics & Toiletries, Jun. 11, 2013, (printed from http://www.cosmeticsandtoiletries.com/formulating/function/moisturizer/premium-Profile-of-Polyquaternium-6-210999891.html on Dec. 6, 2017).*

(Continued)

*Primary Examiner* — Gina C Justice

(57) ABSTRACT

Compositions of the invention contain, in a cosmetically acceptable aqueous medium, a) a cationic polyelectrolyte, b) at least one surfactant; and (c) from about 0.01 to about 1.2 weight percent of an anionic polyelectrolyte, where the weight ratio of the anionic polyelectrolyte to the cationic polyelectrolyte is from about 0.05 to about 1.2, and where the composition exhibits a viscosity change that is below a minimum significant-change-threshold (Δηmin) and exhibits no measurable yield stress or increase in yield stress value when compared to a substantially identical composition that does not contain from about 0.01 to about 1.2 weight percent of the anionic polyelectrolyte, at a weight ratio of anionic polyelectrolyte to cationic polyelectrolyte of from about 0.05 to about 1.2.

12 Claims, No Drawings

(56) References Cited

FOREIGN PATENT DOCUMENTS

| WO | WO 2005/023969 A | 3/2005 |
|---|---|---|
| WO | WO 2006/012465 A | 2/2006 |
| WO | WO 2009/016375 A | 2/2009 |
| WO | WO 2012/054029 A | 4/2012 |
| WO | WO 2014/020081 A | 2/2014 |
| WO | WO 2014/137859 A | 9/2014 |
| WO | WO 2014/144076 A | 9/2014 |
| WO | WO 2015/011380 A | 1/2015 |
| WO | WO 2015/122029 A | 8/2015 |

OTHER PUBLICATIONS

Flick, E., "After-sun moisturizing lotion", Cosmetic and Toiletry Formulations, 1995, 2nd ed., vol. 3, Noyes Publications, p. 753.*

Flick, E., "Styling gel", Cosmetic and Toiletry Formulations, 1989, 2nd ed., vol. 1, Noyes Publications, p. 484.*

EP search report dated Oct. 20, 2017, for EP application 17177186.8.

Bergmann Tiest et al., "Haptic Discrimination and Matching of Viscosity", IEEE Transactions on Haptics, 6, 2013, 24-34.

Bergmann Tiest, "Tactual perception of liquid material properties", Vision Research, 109, 2015, 178-184.

Burgess, Journal of Colloid and Interface Science, vol. 140, No. 1, Nov. 1990, pp. 227-238.

Caelles, et al., "Anionic and Cationic Compounds in Mixed Systems", Cosmetics & Toiletries, vol. 106, Apr. 1991, pp. 49-54.

Klimisch, "Use of Fourier transform infrared spectroscopy with attenuated total reflectance for in vivo quantitation of polydimethylsiloxanes on human skin", Journal of the Society of Cosmetic Chemists, 37, 1986, 73-87.

Lepilleur et al., "Use of statistical modeling to predict the effect of formulation composition on coacervation, silicone deposition, and conditioning sensory performance of cationic cassia polymers", Journal of Cosmetic Science, 62, Mar./Apr. 2011, 161-177.

Stevens et al., "Scaling of Apparent Viscosity", Science, 144, 1964, 1157-1158.

van Oss, Journal of Dispersion Science and Technology, vol. 9 (5,6), 1988-89, pp. 561-573.

Zhou et al., "Phase Behavior of Cationic Hydroxyethyl Cellulose—Sodium Dodecyl Sulfate Mixtures: Effects of Molecular Weight and Ethylene Oxide Side Chain Length of Polymers", Langmuir, 20, 2004, 8482-8489.

International Cosmetic Ingredient Dictionary and Handbook, 15th Edition published by the Personal Care Products Council (PCPC), Washington DC, also available online via the PCPC On-Line Infobase at http://online.personalcarecouncil.org/jsp/Home.jsp.

* cited by examiner

PERSONAL CARE COMPOSITIONS CONTAINING COMPLEXING POLYELECTROLYTES

This application claims the benefit of U.S. Provisional Application 62/352,713 filed Jun. 21, 2016, the complete disclosure of which is hereby incorporated herein by reference for all purposes.

FIELD

The present invention relates to personal care compositions containing complexing polyelectrolyte benefit ingredients.

BACKGROUND

Keratinous surfaces (e.g. skin and hair) are typically cleaned using surfactant-based compositions to remove dirt, soils and excess sebum. However, the cleansing process has disadvantages in that it removes essential/advantageous components from the keratinous surfaces during cleansing. This can lead to an unpleasant feel, e.g., hair can be draggy, entangled and unmanageable, and have a loss of softness and shine, and/or skin or scalp can feel dry, tight and/or itchy and in some cases show redness. Further, it is desirable to provide benefits from cleansing compositions beyond foaming and removal of dirt, soils and excess sebum. A variety of approaches have been developed to alleviate the disadvantages from the cleansing process and to enhance additional benefits beyond foaming and cleansing. For example, cleansing compositions can comprise (in addition to surfactants) oils like silicone oils, vegetable oils and mineral oils to provide e.g. a soft feel and enhanced moisturization to the cleaned surfaces. It is also very common to incorporate cationic components (in most cases cationic polymers) into cleansing compositions to provide enhanced sensorial attributes to the cleaned surfaces, e.g. softness, or improved functional qualities, e.g. detangling and anti-static benefits. These types of additives in cleansing compositions are usually referred to as conditioning agents. Cleansing compositions can also contain additional benefit agents such as zinc pyrithione, salicylic acid or hyaluronic acid. In order for these conditioning agents and the benefit agents to perform, they have to be deposited during the cleansing process onto the surface (e.g. skin and hair).

A common challenge encountered in cleansing compositions is efficacy of deposition of conditioning agents and benefit agents onto the cleaned surfaces. Typically, only a fraction of the agents is deposited and the rest is washed/rinsed off. Keratinous surfaces characteristically have some anionic surface charge; consequently cationic components can adhere to a certain degree onto the keratinous surfaces via electrostatic interaction. Therefore, cationic components, cationic polymers in particular, are used in cleansing compositions as conditioning agents. Through a process typically referred to as "coacervation" or "complexation" or "dilution precipitation", cationic polymers can improve deposition efficacy of conditioning agents such as emollients, oils, other benefit agents and the cationic polymers themselves. In this process, the cationic polymer forms insoluble complexes with anionic surfactant during use of the cleansing composition, i.e. upon dilution. These insoluble complexes or coacervates can enhance deposition efficacy of the cationic polymers as well as water-insoluble components such as oils.

The concept of combining anionic surfactant and cationic polymer is used in many cleansing compositions today. Coacervate formation is dependent upon a variety of criteria such as molecular weight, charge density, pH, and temperature. Coacervate systems and the effect of these parameters have previously been studied and disclosed in, for example, J. Caelles, et al., *Cosmetics & Toiletries*, Vol. 106, April 1991, pp 49-54, C. J. van Oss, *J. Dispersion Science and Technology*, Vol. 9 (5,6), 1988-89, pp 561-573, D. J. Burgess, *J. of Colloid and Interface Science*, Vol. 140, No. 1, November 1990, pp 227-238, S. Zhou et al., *Langmuir*, 20, 2004, 8482-8489, and C. Lepilleur et al., *J. Cosmet. Sci.*, 62, March/April 2011, 161-177. Consequently, approaches to improve the deposition from cleansing compositions include optimization of the cationic polymer as well as of the surfactant system. Optimization of the cationic polymer includes variation of cationic charge density, molecular weight, backbone chemistry and chemistry of the cationic moiety. The surfactant system in the cleansing composition is typically adjusted to the specific cationic polymer utilized to enhance efficiency, compatibility and formulation stability (or vice versa). Several examples of these approaches are disclosed in U.S Pat. Application No. 2003/0108507 and references therein.

However, this reference also discloses a deposition efficacy of only 2-3% (200-300 ppm/% active level in formulation) for small dispersed actives (that is, benefit agent materials that are insoluble in the cleansing formulation and exist as particles or droplets suspended in the cleansing formulation) having a size of less than or equal to 2 μm. A deposition efficacy of only 2-3% shows the general need for improving deposition efficacy from cleanser formulations. Further, the utilization of complexation of anionic surfactants and cationic polymer leads to the deposition of certain amounts of anionic surfactant, present in the coacervate, onto the keratinous surface. This surfactant deposition is undesirable, as anionic surfactants can exhibit high irritation potential when left on skin, and anionic surfactants can denature the keratin components of skin and hair, leading to undesirable morphological changes in these substrates.

Additionally, compositions utilizing complexation of anionic surfactant and cationic polymer typically do not provide any enhancement/aid of depositing water-soluble benefit agents because such benefit agents are not efficiently captured in the polymer-surfactant coacervates upon dilution and thus, are not deposited.

Another approach to enhance deposition efficacy of certain benefit agents described in the prior art is introducing cationic charges to the benefit agents such as emollients, humectants, and waxes. The cationic charges can facilitate adhesion of benefit agents onto surfaces with anionic surface charges such as hair and skin. However, such an approach requires chemical modification of the benefit agent with additional cationic moieties or encapsulation of the benefit agent with cationic materials—both of which may or may not be feasible.

It is reported in the prior art that presence of anionic polymer in compositions with cationic polymer and anionic surfactant does not lead to any improvement of deposition efficacy. For example, anionic rheology modifier polymers like Carbomer and Acrylates Copolymer have been shown to have detrimental effects on deposition efficacy, as e.g. disclosed in WO 2014/137859 A1. Specifically, this reference states that the presence of typical rheology polymers such as anionic acrylic copolymers (e.g. Carbopols) does not improve deposition efficacy of silicone oils. Further, they even severely reduce the deposition efficacy of silicone oils when the silicone oils are of smaller particle size (e.g. average oil droplet size of less than 5 micrometers). This reference further states that the "silicone deposition is inversely proportional to the amount of the acrylic stabilizer thickener present". The reference discloses the use of a nonionic amphiphilic rheology modifying polymer to stabilize the composition "without interfering with the deposition of the silicone material" and is silent on how to improve deposition efficacy.

In summary, despite the various approaches used in the prior art to improve conditioning and deposition efficacy from cleansing formulations, there still remain disadvantages to the prior art, such as: low deposition efficacy, potential irritation from deposition of surfactant, limited compatibility with anionic polymers, and lack of aid in deposition of water-soluble components other than surfactants. As such, it remains desirable to provide improved cleansing compositions with optimum performance and enhanced deposition efficacy.

SUMMARY OF THE INVENTION

The present invention provides compositions comprising, in a cosmetically acceptable aqueous medium, a) a cationic polyelectrolyte, b) at least one surfactant; and c) from about 0.01 weight percent to about 1.2 weight percent of an anionic polyelectrolyte. The weight ratio of anionic polyelectrolyte to cationic polyelectrolyte is from about 0.05 to about 1.2. Compositions of the present invention exhibit a viscosity change that is below a minimum significant-change-threshold ($\Delta\eta_{min}$) and exhibit no measurable yield stress or increase in yield stress value when compared to a substantially identical composition that does not contain from about 0.01 weight percent to about 1.2 weight percent of the anionic polyelectrolyte, at a weight ratio of anionic polyelectrolyte to cationic polyelectrolyte of from about 0.05 to about 1.2.

DETAILED DESCRIPTION OF THE INVENTION

Cleansing compositions of the present invention comprise combinations of cationic and anionic polyelectrolytes. The amount of anionic polyelectrolyte is selected such that the anionic polyelectrolyte is sufficient to increase the amount of Dry Precipitate Mass Yield upon dilution and maintain effective cleansing efficacy without the undesired effect of changing the rheology properties of the composition. If the weight ratio of anionic polyelectrolyte to cationic polyelectrolyte is from about 0.05 to about 1.2, the anionic polyelectrolytes do not increase the Dry Precipitate Mass Yield.

The specific combination of the anionic polyelectrolyte(s) and the cationic polyelectrolyte(s) in a surfactant system as described herein is referred to as the "Polyelectrolyte Conditioning System". "Polyelectrolyte Conditioning System", as used herein, means a combination of anionic polyelectrolyte(s) and cationic polyelectrolyte(s), where the anionic and cationic polyelectrolyte(s) are present at a weight ratio of anionic polyelectrolyte to cationic polyelectrolyte of from about 0.05 to about 1.2, and the concentration of the anionic polyelectrolyte based on total weight of the cleansing composition is from about 0.01 to about 1.2 wt %.

Compositions of the present invention that contain such a Polyelectrolyte Conditioning System exhibit an improved deposition efficacy of conditioning agents and benefit agents, compared to similar compositions that do not include such a Polyelectrolyte Conditioning System, as well as provide additional benefits, e.g. a modified skin feel after application or a reduced amount of deposited surfactant. Preferred weight ratios of anionic to cationic polyelectrolyte include from about 0.05 to about 1.2, or from about 0.1 to about 1.2, or from about 0.1 to about 1. The presence of the anionic polyelectrolyte within the specific range increases the Dry Precipitate Mass Yield upon dilution, measured as described below, by 10% or more compared to a substantially identical composition that does not contain such an amount of anionic polyelectrolyte. More preferably the Dry Precipitate Mass Yield upon dilution is increased by 20% or more, or even more preferably by 40% or more.

As noted above, the weight ratio of anionic polyelectrolyte to cationic polyelectrolyte is crucial. Typically, at ratios of about 0.05 to about 1.2, the compositions exhibit an increased Dry Precipitate Mass Yield upon dilution. Depending on the type of polyelectrolytes, the surfactant system and other formulation parameters, e.g. salt level, the optimal weight ratio of anionic to cationic polyelectrolyte to achieve the maximum Dry Precipitate Mass Yield may vary within this range. An increase in the Dry Precipitate Mass Yield upon dilution of a cleansing composition is an indication of an improved efficacy in deposition of conditioning agents and benefit agents. Further, an increase in the Dry Precipitate Mass Yield is an indication that the anionic polyelectrolyte is part of the coacervates formed upon dilution and, thus, is also deposited. However, incorporating too much anionic polyelectrolyte into the composition, compared to the cationic polyelectrolyte, i.e. when the ratio of anionic polyelectrolyte mass to cationic polyelectrolyte mass is greater than about 1.2, results in no improvement, or even a decrease in performance, compared to the composition with no anionic polyelectrolyte.

Where applicable, chemicals are specified according to their INCI Name. Additional information, including suppliers and trade names, can be found under the appropriate INCI monograph in the *International Cosmetic Ingredient Dictionary and Handbook*, 15$^{th}$ Edition published by the Personal Care Products Council (PCPC), Washington D.C., also available online via the PCPC On-Line Infobase at http://online.personalcarecouncil.org/jsp/Home.jsp.

All percentages listed in this specification are percentages by weight, unless otherwise specifically mentioned. Percentages and weights of components like polyelectrolyte, surfactant, salt, polymers, acids etc. listed in this specification are percentages and weights of active matter of a component excluding e.g. solvents like the water of an aqueous sodium chloride solution added to a composition.

As used herein, "substantially identical composition" means a composition that is substantially the same as compositions of the present invention, but for the relative amounts of anionic polyelectrolyte and cationic polyelectrolyte.

As used herein, "wt %" refers to weight percent, i.e. % weight/weight; e.g. 5 g Sodium Chloride in 95 g water is 5 wt % active Sodium Chloride in aqueous solution.

Anionic Polyelectrolyte

An anionic polyelectrolyte is a polymer bearing a plurality of anionic charges, i.e. the polyelectrolyte contains monomers or repeat units bearing anionic moieties. Suitable moieties bearing anionic charge can be, but are not limited to $CO_2^-$, $SO_3^-$, $SO_4^-$, $PO_3^{2-}$, and $PO_4^{2-}$. Compositions of the present invention contain from about 0.01 wt % to about 1.2 wt % anionic polyelectrolyte.

The anionic polyelectrolyte has a charge density of about 0.1 milliequivalents per gram (meq/g) or more, more preferably from about 0.1 to 10 meq/g, even more preferably from about 0.5 to 5 meq/g and even more preferably from about 0.5 to 4 meq/g and a weight average molecular weight (Mw) of about 10,000 g/mol or more, more preferably from about 50,000 g/mol or more. For non-crosslinked anionic polyelectrolytes the molecular weight is from about 50,000 to 3,000,000 g/mol and more preferably from about 50,000 g/mol to 1,000,000 g/mol. Cross-linked polyelectrolytes are typically defined by their primary particle size rather than a molecular weight. Preferred primary particle sizes for cross-linked anionic polyelectrolytes are about 0.01 micrometer (µm) or more, more preferred about 0.1 µm or more, and 1000 µm or less, more preferred about 100 µm or less. Examples for cross-linked anionic polyelectrolytes are, e.g. Acrylates Copolymer like Carbopol® Aqua SF-1, with a primary particle size of about 0.2 µm, and polyacrylate super absorbent polymer particles with sizes of about 25-500 µm.

Suitable anionic polyelectrolytes include, but are not limited to, 1) polyelectrolytes derived from ethylenically unsaturated monomers containing anionic or anionically ionizable monomers, 2) anionic and anionically ionizable polysaccharides and polysaccharide derivatives and 3) other anionic polyelectrolytes such as anionic/anionically ionizable polypeptides/proteins, anionic/anionically ionizable hybrid (co)polymers containing natural polymer chains (like e.g. polysaccharide or protein chains) as well as synthetic polymer chains (like e.g. polyethylene glycol or acrylate (co)polymer).

Non limiting examples of such polyelectrolytes are described under the appropriate INCI monographs in the *International Cosmetic Ingredient Dictionary and Handbook*, 15$^{th}$ Edition published by the Personal Care Products Council (PCPC), Washington D.C.

Polyelectrolytes derived from ethylenically unsaturated monomers containing anionic/anionically ionizable monomers include, but are not limited to (a) linear non-crosslinked (co)polymers, including non-crosslinked alkali-swellable emulsion (ASE) polymers, (b) crosslinked (co)polymers, including crosslinked ASE polymers (xASE), and (c) hydrophobically modified derivatives of (co)polymers described under (a) and (b), including non-crosslinked and crosslinked hydrophobically modified alkali-swellable emulsion (HASE and xHASE) polymers.

Examples of anionic/anionically ionizable ethylenically unsaturated monomers include acrylic acid, methacrylic acid, vinyl sulfonic acid, vinyl sulfuric acid, vinyl phosphonic acid, vinyl phosphoric acid, vinyl boronic acid, citraconic acid, maleic acid, fumaric acid, crotonic acid, itaconic acid, methacryloxyethyl phosphate, methacryloxyethyl sulfuric acid, methacryloxyethyl sulfonic acid and 2-acrylamidomethylpropane sulfonic acid (AMPSA), 2-methyl-2-propenoic acid ethyl-2-phosphate ester (HEMA-phosphate), methacryloyloxy PPG-7 phosphate, beta-carboxyethyl acrylate, 3-acrylamido-3-methylbutanoic acid (AMBA), and mixtures thereof.

As used herein, the term "(co)polymer" is meant to include polyelectrolytes derived from essentially one type of monomer (homopolymer) as well as polyelectrolytes derived from more than one type of monomer copolymer).

The anionic polyelectrolytes derived from ethylenically unsaturated monomers of the invention can be synthesized via free radical polymerization techniques known in the art. In another aspect bulk polymerization, solvent polymerization, precipitation polymerization, or emulsion polymerization techniques can be used to synthesize the anionic polyelectrolytes of the invention derived from ethylenically unsaturated monomers.

As used herein the term "linear non-crosslinked (co)polymer" of the invention, refers to an anionic polyelectrolyte made from ethylenically unsaturated monomers, containing one or more anionic/anionically ionizable ethylenically unsaturated monomers and optionally one or more nonionic or amphoteric ethylenically unsaturated monomers. Examples for nonionic or amphoteric ethylenically unsaturated monomers include, but are not limited to ethyl (meth)acrylate, butyl (meth)acrylate, vinyl formate, vinyl acetate, 1-methylvinyl acetate, vinyl propionate, vinyl butyrate, (meth)acrylamide, dimethyl acrylamide, sulfobetaine acrylates, e.g. 3-methacrylamidopropyldimethylammonio propanesulfonate, and mixtures thereof. Examples of anionic linear non-crosslinked (co)polymers include, but are in no way limited to poly(meth)acrylic acid homopolymers or acrylamide-(meth)acrylic acid copolymers. As used herein, the term "(meth)acrylic" acid is meant to include the corresponding methyl derivatives of acrylic acid, and "(meth)acrylate" is meant to include the corresponding methyl derivatives of alkyl acrylate and salt forms of acrylic acid. For example, "(meth)acrylic" acid refers to acrylic acid and/or methacrylic acid and "(meth)acrylate" refers to alkyl acrylate and/or alkyl methacrylate and "sodium (meth)acrylate" refers to sodium acrylate and/or sodium methacrylate. The linear non-crosslinked (co)polymer is not hydrophobically modified.

As used herein the term "crosslinked (co)polymer" of the invention refers to a crosslinked anionic polyelectrolyte made from ethylenically unsaturated monomers. Specifically, it is a crosslinked derivative of a linear non-crosslinked (co)polymer as described above. Crosslinking may be achieved via a variety of techniques known to those skilled in the art, e.g. copolymerization with multifunctional ethylenically unsaturated monomers or post-polymerization reactions to induce crosslinking. Examples include, but are not limited to, Carbomers and acrylates crosspolymers. Examples for Carbomers are Carbopol® 934, 940, 980, Ultrez 10, Ultrez 30, ETD2050, 2984 from Lubrizol, Inc. or Ashland® 940, 941, 980, 981 from Ashland, Inc. An example for acrylates crosspolymer is Acrylates Crosspolymer-4 (Carbopol® Aqua SF-2 from Lubrizol, Inc.). Other examples include superabsorbent polymers, i.e. crosslinked sodium polyacrylate particles.

As used herein the term "hydrophobically modified (co)polymers", refers to linear non-crosslinked and crosslinked (co)polymer containing hydrophobic monomers. Specifically, "hydrophobically modified" means that the polyelectrolyte contains some amount of monomer(s) containing a hydrophobic side group (a hydrophobic monomer, or also referred to as associative monomer). Typically, the amount of monomer(s) containing a hydrophobic side group is from about 0.1 wt % to about 20 wt %, more typically about 0.5 wt % to about 10 wt %, and even more typically from about 1 wt % to about 5 wt %. They may optionally contain a crosslinker and/or may optionally be a crosslinked (co)polymer. Examples are Acrylates/C10-30Alkyl Acrylate Crosspolymers (Carbopol® ETD2020, Ultrez 20 from Lubrizol, Inc.) and Acrylates/Vinyl Isodecanoate Crosspolymer (Stabylen 30 from 3V Sigma, Inc.).

"Non-hydrophobically modified" as used herein, means that the polyelectrolyte has no or only minor amounts of monomers containing a hydrophobic side group (a hydrophobic monomer, or also referred to as associative monomer). Typically, the amount of monomer(s) containing a hydrophobic side group is about 1 wt % or lower, more typically about 0.5 wt % or lower, and even more typically about 0.1 wt % or lower. Exceptions are crosslinker monomers/molecules, which may have side chains with greater than 4 carbon atoms, but are not considered a hydrophobic monomer (and their use level in the polyelectrolyte is typically low, i.e. less than 1 wt %).

As used herein the term "alkali-swellable emulsion polymer" or "ASE polymer", refers to a polyelectrolyte made from ethylenically unsaturated monomers, e.g. being an acrylate or vinyl (co)polymer, and wherein the polymer contains anionically-ionizable monomers such that they become ionized and swell and/or dissolve in aqueous solutions upon addition of base (alkali). The ASE polymer may optionally contain a crosslinker and/or may optionally be a crosslinked polymer (xASE). In one embodiment, the ASE or xASE polymer is an acrylates (co)polymer consisting of one or more monomers of (meth)acrylic acid and/or one of their simple alkyl-esters (including methyl-, ethyl-, propyl-, butyl-ester) and simple hydroxyalkyl-esters (including hydroxyethyl-ester, hydroxybutyl-ester) and simple alkoxy-alkyl-esters (including methoxyethyl-ester, ethoxyethyl-ester). "Simple" alkyl ester refers to the alkyl-group having from 1 to 4 carbons. The amount of simple alkyl ester (meth)acrylate monomer in the polymer ranges from 0-80 wt %, 10-70 wt %, 20-70 wt %, 30-70 wt %, 30-60 wt %. Specific examples of simple alkyl ester (meth)acrylate monomers include methyl(meth)acrylate, ethyl(meth)acrylate, butyl (meth)acrylate, isobutyl(meth)acrylate, hydroxyethyl(meth)acrylate, hydroxypropyl(meth)acrylate, methoxyethyl(meth)acrylate, ethoxyethyl (meth)acrylate. Examples of ASE polymers are Acrylates Copolymer (e.g. Carbopol® Aqua SF-1 from Lubrizol, Inc, or Eliclear™ 4U from Seppic, Inc.) or Potassium Acrylates Copolymer (EX-968 and EX-1112 from Lubrizol, Inc.).

As used herein the term "hydrophobically modified alkali swellable emulsion polymer" or "HASE polymer", including "xHASE polymer", refers to ASE polymers and xASE polymers, respectively, containing hydrophobic monomers (see above for definition of "hydrophobically modified"). Example of a HASE polymer is Polyacrylate-33 (Rheomer™ 33 from Solvay, Inc.) and for xHASE e.g. Acrylates/Steareth-20 Methacrylate crosspolymer (Aculyn™ 88 from Dow, Inc.).

Hydrophobic monomers (also referred to as "associative" monomers) used in hydrophobically modified polyelectrolytes are described for example in U.S. Pat. No. 5,292,843, U.S. Pat. No. 6,897,253, U.S. Pat. No. 7,288,616, U.S. Pat. No. 3,035,004, and U.S. Patent Publication No. 2006/0270563, the contents each of which is hereby incorporated by reference in their entirety.

As used herein, the term "non-crosslinked" refers to a (co)polymer that is substantially free of covalent bond linkages between polymer chains.

As used herein, the term "crosslinked" refers to a (co)polymer with some amounts of covalent bond linkages between polymer chains. Such bond linkages are generated by addition of some amounts of crosslinking monomers to the (co)polymer during the polymerization process. Examples of crosslinkers are allyl ethers of pentaerythritol, allyl ethers of sucrose, or allyl ethers of propylene, or trimethylolpropane triacrylate, ethylene glycol dimethacrylate. Additional crosslinkers are described in U.S. Pat. No. 9,187,590 B2, the contents of which are incorporated herein by reference.

The anionic polyelectrolyte derived from ethylenically unsaturated monomers can also contain other monomers. For example, vinyl esters such as: vinyl acetate, vinyl propionate, N-vinylamides such as: N-vinylpyrrolidione, N-vinylcaprolactam, N-vinylformamide, and N-vinylacetamide, and vinyl ethers such as: methyl vinyl ether, ethyl vinyl ether, butyl vinyl ether, and hydroxybutyl vinyl ether, and ethylenically unsaturated aryl compounds, such as: styrene, acetoxyethyl (meth)acrylate, and (meth)acrylamides such as: (meth)acrylamide, dimethylacrylamide, N-methylol (meth)acrylamide, N-butoxyethyl(meth)acrylamide, N,N-dimethyl (meth)acrylamide, N-isopropyl(meth)acrylamide, N-test-butyl (meth)acrylamide, and ethylenically unsaturated alkyl esters of dicarboxylic acid monomers, such as: butyl methyl maleate.

Anionic and anionically modified polysaccharides and polysaccharide derivatives include, but are not limited to:
a. naturally occurring anionic polysaccharides: alginates (alginic acid), pectin, carrageenan, xanthan, hyaluronic acid, chondroitin sulfate, gum Arabic, gum karaya, gum traganth, arabinoxylans, heparan sulfate, and
b. anionically modified polysaccharides: include starches, gums, cellulosics such as carboxy methyl starch, starch phosphate, hydroxypropyl starch phosphate, starch sulfate, starch-2-hydroxypropylcitrate, carboxymethyl guar, carboxymethyl hydroxypropyl guar, other anionic galactomannan derivatives, carboxy methyl cellulose (INCI name: Cellulose Gum), e.g. as Aqualon™ Sodium CMC from Ashland, Inc., or as Walocel™ CRT from Dow, Inc., polyanionic cellulose, cellulose sulfate, cellulose phosphate, and carboxyethyl cellulose, and other polysaccharides like e.g. dextran and dextrin, like e.g. dextran/dextrin sulfate.

Other anionic polyelectrolytes include anionic/anionically ionizable proteins, anionic polypeptides, e.g., polyglutamic acid, polyaspartic acid, and other anionic copolymers such as polynucleic acids.

Cationic Polyelectrolyte

A cationic polyelectrolyte is a polymer bearing a plurality of cationic charges, i.e. the polyelectrolyte contains repeat units bearing cationic moieties. Suitable cationic polyelectrolytes for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polyelectrolytes so long as the polyelectrolytes remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate, methylsulfate, and ethylsulfate, citrate, acetate, and lactate.

Compositions of the present invention contain from about 0.1 wt % to about 1 wt % cationic polyelectrolyte, more preferably from about 0.1 wt % to about 0.8 wt %.

Preferred cationic polyelectrolytes used in the compositions of the present invention have cationic charge densities of at least about 0.2 meq/g, preferably at least about 0.6 meq/g, more preferably at least about 1.5 meq/g, but also preferably less than about 7 meq/g, more preferably less than about 5 meq/g, and even more preferably less than about 3 meq/g, at a pH range intended for use of the composition. The "cationic charge density" of a polyelectrolyte, as that term is used herein, refers to the ratio of the number of positive charges on the polyelectrolyte to the molecular weight of the polyelectrolyte. The weight average molecular weight (Mw) of such suitable cationic polyelectrolytes will generally be between about 10,000 and about 5 million g/mol, preferably between about 50,000 and about 5 million g/mol, more preferably between about 100,000 and about 3 million g/mol. The cationic polyelectrolyte may be a cross-linked (co)polymer.

Non limiting examples of such cationic polyelectrolytes are described under the appropriate INCI monographs in the *International Cosmetic Ingredient Dictionary and Handbook, 15th Edition* published by the Personal Care Products Council (PCPC), Washington D.C., the contents of which is incorporated herein by reference.

Non limiting examples of suitable cationic polyelectrolytes include copolymers of ethylenically unsaturated monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polyelectrolytes of the composition herein, include ethylenically unsaturated compounds substituted with dialkylaminoalkyl acrylate, dialkylaminoalkyl methacrylate, monoalkylaminoalkyl acylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polyelectrolytes for use in the compositions include copolymers of 1-vinyl-2-pyrrolidone and 1-vinyl-3-methylimidazolium salt (e.g. chloride salt) (INCI name: Polyquarternium-16); copolymers of 1-vinyl-2-pyrrolidone and dimethylaminoethyl methacrylate (INCI name: Polyquarternium-11); copolymers of vinylpyrrolidone and quaternized vinylimidazolium salts (INCI name: Polyquarternium-44); copolymers of vinylpyrrolidone and methacrylamidopropyltrimethylammonium chloride (INCI name: Polyquarternium-28); copolymers of methacryloyloxyethyl trimethyl ammonium methylsulfate (METAMS) and acrylamide (INCI name: Polyquarternium-5); cationic diallyl quaternary ammonium-containing polymers, including, for example, dimethyldiallylammonium chloride homopolymer, copolymers of acrylamide and dimethyldiallylammonium chloride (INCI name: Polyquarternium-6 and Polyquarternium-7, respectively), amphoteric copolymers of acrylic acid including copolymers of acrylic acid and dimethyldiallylammonium chloride (NCI name: Polyquarternium-22), polyampholyte (co)polymers such as polybetaines and polysulfobetaines, terpolymers of acrylic acid with dimethyldiallylammonium chloride and acrylamide (INCI name: Polyquarternium-39), and terpolymers of acrylic acid with methacrylamidopropyl trimethylammonium chloride and methylacrylate (INCI name: Polyquarternium-47). Preferred cationic substituted monomers are the cationic substituted dialkylaminoalkyl acrylamides, dialkylaminoalkyl methacrylamides, and combinations thereof. A non-limiting specific example is Polymethyacrylamidopropyl Trimonium Chloride. Also preferred are copolymers of the cationic monomer with nonionic monomers such that the charge density of the total copolymers is about 0.6 to about 5 meq/gram.

Other suitable cationic polyelectrolytes for use in the composition include polysaccharide polymers, such as cationic cellulose derivatives and cationic starch derivatives. Suitable cationic polysaccharide polymers include those which conform to the formula:

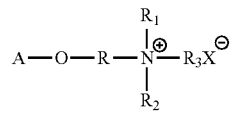

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less, more preferably about 10 or less; and X is an anionic counterion as described in hereinbefore. In one preferred embodiment, R is 2-hydroxypropyl and $R_1$, $R_2$, and $R_3$ are methyl.

Preferred cationic cellulose polymers are salts of hydroxyethyl cellulose reacted with trimethyl ammonium substituted epoxide (INCI name: Polyquarternium-10). Other suitable types of cationic cellulose include the polymeric quaternary ammonium salts of hydroxyethyl cellulose reacted with lauryl dimethyl ammonium-substituted epoxide (INCI name: Polyquarternium-24) and reacted with lauryl dimethylammonium- and trimethylammonium-substituted epoxide (INCI name: Polyquarternium-67).

Other suitable cationic polyelectrolytes include cationic galactomannans such as cationic tara gum, cassia gum and guar gum derivatives, such as Guar Hydroxypropyltrimonium Chloride, specific examples of which include the Jaguar series commercially available from Solvay, Inc. and the N-Hance series commercially available from Ashland, Inc. Other suitable cationic polyelectrolytes include quaternary nitrogen-containing cellulose ethers, some examples of which are described in U.S. Pat. No. 3,962,418, which description is incorporated herein by reference. Other suitable cationic polyelectrolytes include copolymers of etherified cellulose, guar and starch, some examples of which are described in U.S. Pat. No. 3,958,581, the contents of which is incorporated herein by reference. Other suitable conditioning polymers include those disclosed in U.S. Pat. No. 5,876,705, the contents of which is incorporated herein by reference. When used, the cationic polyelectrolytes herein are either soluble in the composition or are soluble in a complex coacervate phase in the composition formed by the cationic polyelectrolyte and the anionic, amphoteric and/or zwitterionic detersive surfactant component described hereinbefore.

Other suitable cationic polyelectrolytes may include proteins bearing cationic charges, like gelatin, ovalbumin, serum albumin, casein and hydrolyzed wheat or rice or silk protein substituted with hydroxypropyltrimonium moieties and cationic polypeptides, such as poly(L-lysine), poly(L-arginine), abaecin, propenin, or indolicidin.

Other suitable cationic polyelectrolytes include linear and branched polyethyleneimine (PEI) (co)polymers. Examples include PEI-2500, PEI-14M.

Generally, it is recognized that the cationic polyelectrolytes exist in the cleansing composition as a coacervate phase or form a coacervate phase upon dilution. If not already a coacervate in the cleansing composition, the cationic polyelectrolyte will preferably exist in a complex coacervate form in the cleansing composition upon dilution with water to a weight ratio of water to composition of about 20:1, more preferably at about 10:1, even more preferably at about 5:1, and even more preferably at about 3:1.

Surfactants

Compositions of the present invention contain from about 1 wt % to about 25 wt % surfactant, more preferably from about 3 wt % to about 25 wt % surfactant, more preferably from about 3 wt % to about 15 wt %, even more preferable from about 3 wt % to about 12 wt % and even more preferably from about 4 wt % to about 12 wt %.

Suitable surfactants may be anionic, zwitterionic, nonionic and cationic surfactants, examples of which are described below.

As used herein, the term "anionic surfactant" refers to a surfactant molecule bearing at least a negative charge and no positive charge besides counterion(s), $M^+$. Suitable anionic surfactants include those selected from the following classes of surfactants:

Acyl isethionates

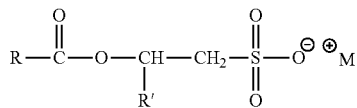

where $RCO=C_8-C_{20}$ acyl (linear or branched, saturated or unsaturated) or mixtures thereof, $R'=H$ or $CH_3$, $M^+=$monovalent cation, such as Sodium Cocoyl Isethionate (RCO=coco acyl, $R'=H$, $M^+=Na^+$) and Sodium Lauroyl Methyl Isethionate (RCO=lauroyl, $R'=CH_3$, $M^+=Na^+$).

Alkyl sulfosuccinates

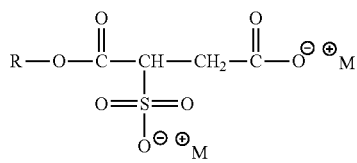

where $R=C_8-C_{20}$ alkyl (linear or branched, saturated or unsaturated) or mixtures thereof and $M^+=$monovalent cation, such as Disodium Lauryl Sulfosuccinate (R=lauryl, $M^+=Na^+$).

α-Sulfo fatty acid esters

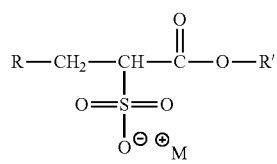

where $R=C_6-C_{16}$ alkyl (linear or branched, saturated or unsaturated) or mixtures thereof, $R'=C_1-C_2$ alkyl, and $M^+=$monovalent cation, such as Sodium Methyl 2-Sulfolaurate ($R=C_{10}H_{21}$, $R'=$methyl, $CH_3$, and $M^+=Na^+$);

α-Sulfo fatty acid salts

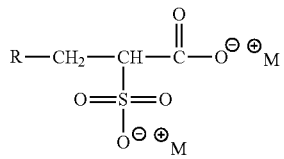

where $R=C_6-C_{16}$ alkyl (linear or branched, saturated or unsaturated) or mixtures thereof, $M^+=$monovalent cation, such as Disodium 2-Sulfolaurate ($R=C_{10}H_{21}$, $M^+=Na^+$);

Alkyl sulfoacetates

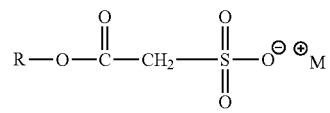

where $R=C_6-C_{18}$ alkyl (linear or branched, saturated or unsaturated) or mixtures thereof, $M^+=$monovalent cation, such as Sodium Lauryl Sulfoacetate (R=lauryl, $C_{12}H_{25}$, $M^+=Na^+$).

Alkyl sulfates

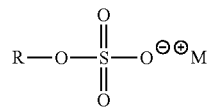

where $R=C_8-C_{20}$ alkyl (linear or branched, saturated or unsaturated) or mixtures thereof. Specific examples include TEA-Lauryl Sulfate (R=lauryl, $C_{12}H_{25}$, $M^+=^+HN(CH_2CH_2OH)_3$), Sodium Lauryl Sulfate (R=lauryl, $C_{12}H_{25}$, $M^+=Na^+$), and Sodium Coco-Sulfate (R=coco alkyl, $M^+=Na^+$).

Alkyl glyceryl ether sulfonates or alkoxyl hydroxypropyl sulfonates:

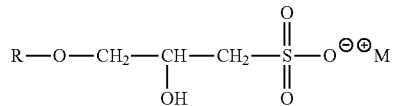

where $R=C_8-C_{24}$ alkyl (linear or branched, saturated or unsaturated) or mixtures thereof and $M^+=$monovalent cation, such as Sodium Cocoglyceryl Ether Sulfonate (R=coco alkyl, $M^+=Na^+$);

Alpha olefin sulfonates (AOS) prepared by sulfonation of long chain alpha olefins. Alpha olefin sulfonates consist of mixtures of alkene sulfonates,

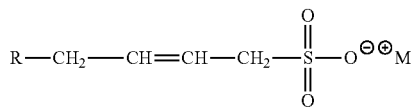

where $R=C_4-C_{15}$ alkyl or mixtures thereof and $M^+=$monovalent cation, and hydroxyalkyl sulfonates,

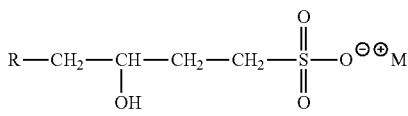

where R=$C_4$-$C_{18}$ alkyl or mixtures thereof and $M^+$=monovalent cation. Examples include Sodium $C_{12-14}$ Olefin Sulfonate (R=$C_8$-$C_{10}$ alkyl, $M^+$=$Na^+$) and Sodium C14-16 Olefin Sulfonate (R=$C_{10}$-$C_{12}$ alkyl, $M^+$=$Na^+$);

Alkyl sulfonates or paraffin sulfonates:

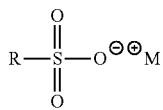

where R=$C_8$-$C_{24}$ alkyl (linear or branched, saturated or unsaturated) or mixtures thereof and $M^+$=monovalent cation. Examples include Sodium C13-17 Alkane Sulfonate (R=$C_{13}$-$C_{17}$ alkyl, $M^+$=$Na^+$) and Sodium C14-17 Alkyl Sec Sulfonate (R=$C_{14}$-$C_{17}$ alkyl, $M^+$=$Na^+$);

Alkylaryl sulfonates or linear alkyl benzene sulfonates

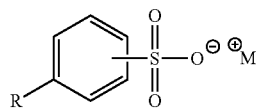

where R=$C_6$-$C_{18}$ alkyl (linear, saturated or unsaturated) or mixtures thereof and $M^+$=monovalent cation. Examples include Sodium Deceylbenzenesulfonate (R=$C_{10}$ alkyl, $M^+$=$Na^+$) and Ammonium Dodecylbenzensulfonate (R=$C_{12}$ alkyl, $M^+$=$NH_4^+$);

Alkyl ether sulfates

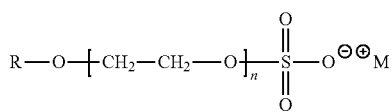

where R=$C_8$-$C_{24}$ alkyl (linear or branched, saturated or unsaturated) or mixtures thereof, n=1-12, and $M^+$=monovalent cation. Examples include Sodium Laureth Sulfate (R=$C_{12}$ alkyl, $M^+$=$Na^+$, n=1-3), Ammonium Laureth Sulfate (R=$C_{12}$ alkyl, $M^+$=$NH_4^+$, n=1-3), and Sodium Trideceth Sulfate (R=$C_{13}$ alkyl, $M^+$=$Na^+$, n=1-4);

Alkyl monoglyceride sulfates

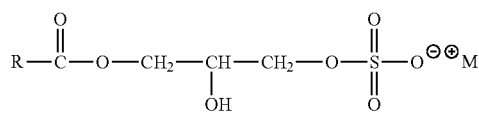

where RCO=$C_8$-$C_{24}$ acyl (linear or branched, saturated or unsaturated) or mixtures thereof and M=monovalent cation. Examples include Sodium Cocomonoglyceride Sulfate (RCO=coco acyl, $M^+$=$Na^+$) and Ammonium Cocomonoglyceride Sulfate (RCO=coco acyl, $M^+$=$NH_4$);

Alkyl ether carboxylates

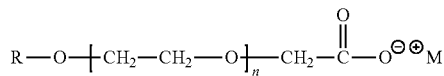

where R=$C_8$-$C_{24}$ alkyl (linear or branched, saturated or unsaturated) or mixtures thereof, n=1-20, and $M^+$=monovalent cation. Examples include Sodium Laureth-13 Carboxylate (R=$C_{12}$ alkyl, $M^+$=$Na^+$, n=13), and Sodium Laureth-3 Carboxylate (R=$C_{12}$ alkyl, $M^+$=$Na^+$, n=3);

Alkyl ether sulfosuccinates

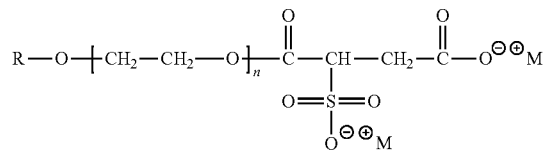

where R=$C_8$-$C_{20}$ alkyl (linear or branched, saturated or unsaturated) or mixtures thereof, n=1-12, and $M^+$=monovalent cation, such as Disodium Laureth Sulfosuccinate (R=lauryl, n=1-4, and $M^+$=$Na^+$)

Dialkyl sulfosuccinates

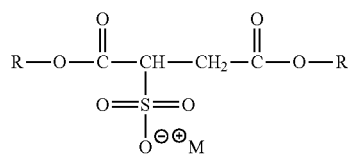

where R=$C_6$-$C_{20}$ alkyl (linear or branched, saturated or unsaturated) or mixtures thereof and $M^+$=monovalent cation, such as Diethylhexyl Sodium Sulfosuccinate (R=2-ethylhexyl, $M^+$=$Na^+$).

Alkylamidoalkyl sulfosuccinates

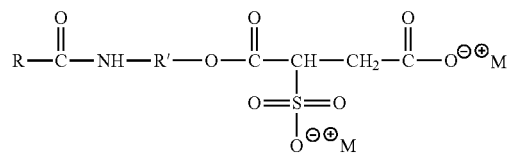

where R=$C_8$-$C_{20}$ alkyl (linear or branched, saturated or unsaturated) or mixtures thereof, R'=$C_2$-$C_4$ alkyl (linear or branched), and $M^+$=monovalent cation, such as Disodium Cocamido MIPA-Sulfosuccinate (RCO=coco acyl, R'=isopropyl, $M^+$=$Na^+$).

Alkyl sulfosuccinamates

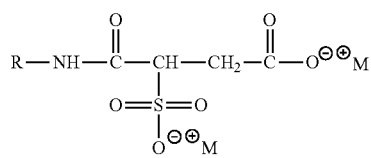

where R=$C_8$-$C_{20}$ alkyl (linear or branched, saturated or unsaturated) or mixtures thereof and $M^+$=monovalent cation, such as Disodium Stearyl Sulfosuccinamate (R=stearyl, $C_{18}H_{37}$, $M^+$=$Na^+$).

Acyl glutamates

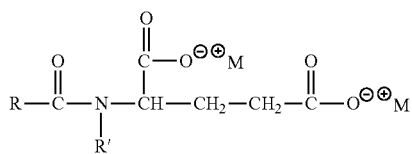

where RCO=$C_6$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, $M^+$=$Na^+$) and Disodium Lauroyl Glutamate (RCO=lauroyl, R'=H, $M^+$=$Na^+$).

Acyl aspartates

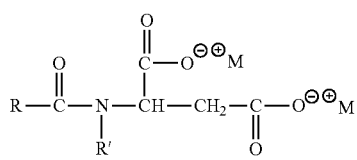

where RCO=$C_6$-$C_{20}$ acyl (linear or branched, saturated or unsaturated) or mixtures thereof, R'=H or $CH_3$, $M^+$=monovalent cation, such as Disodium N-Lauroyl Aspartate (RCO=lauroyl, R'=H, $M^+$=$Na^+$).

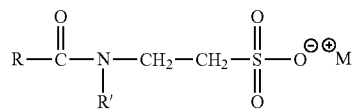

where RCO=$C_6$-$C_{20}$ acyl (linear or branched, saturated or unsaturated) or mixtures thereof, R'=H or $CH_3$, $M^+$=monovalent cation, such as Sodium Methyl Cocoyl Taurate (RCO=coco acyl, R'=$CH_3$, $M^+$=$Na^+$) and Sodium Cocoyl Taurate (RCO=lauroyl, R'=H, $M^+$=$Na^+$).

Acyl lactylates

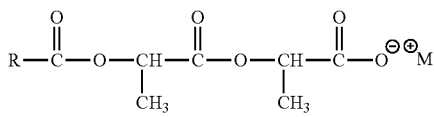

where RCO=$C_8$-$C_{20}$ acyl (linear or branched, saturated or unsaturated) or mixtures thereof, $M^+$=monovalent cation, such as Sodium Lauroyl Lactylate (RCO=lauroyl, $M^+$=$Na^+$).

Acyl glycinates and acyl sarcosinates

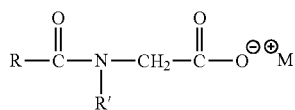

where RCO=$C_8$-$C_{20}$ acyl (linear or branched, saturated or unsaturated) or mixtures thereof, R'=H (glycinate) or $CH_3$ (sarcosinate), $M^+$=monovalent cation, such as Sodium Cocoyl Glycinate (RCO=coco acyl, R'=H, $M^+$=$Na^+$), Ammonium Cocoyl Sarcosinate (RCO=coco acyl, R'=$CH_3$, $M^+$=$NH_4^+$) and Sodium Lauroyl Sarcosinate (RCO=lauroyl, R'=$CH_3$, $M^+$=$Na^+$).

Anionic derivatives of alkyl polyglucosides, including: Sodium Lauryl Glucoside Carboxylate, Disodium Coco-Glucoside Citrate, Sodium Coco-Glucoside Tartrate, Disodium Coco-Glucoside Sulfosuccinate; Sodium Cocoglucosides Hydroxypropylsulfonate, Sodium Decylglucosides Hydroxypropylsulfonate, Sodium Laurylglucosides Hydroxypropylsulfonate; Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer; Anionic polymeric APG derivatives, such as those described in O'Lenick, U.S. Pat. Nos. 7,507,399; 7,375,064; and 7,335,627; and combinations of two or more thereof, and the like.

As used herein, the term "sulfated anionic surfactant" refers to anionic surfactants containing a —$SO_4^-M^+$ group, with $M^+$ being absent, or $H^+$ or $NH_4^+$ or $Na^+$ or $K^+$ or other monovalent or multivalent anion. Examples of sulfated anionic surfactants include, but are not limited to, sodium lauryl sulfate and sodium laureth sulfate. In certain embodiments, the compositions of the present invention are essentially free of sulfated anionic surfactant, and preferably are free of sulfated anionic surfactant.

In certain embodiments, the compositions of the present invention are essentially free of anionic surfactant, and preferably are free of anionic surfactant.

In certain embodiments of the present invention, the composition may comprise a zwitterionic surfactant. Suitable concentrations of zwitterionic surfactant are from about 0 wt % to 15 wt %, preferably from about 1-10 wt %, more preferably from about 2 wt % to 6 wt %.

In certain embodiments, the compositions of the present invention contain one or more anionic and one or more zwitterionic surfactant(s). Ratios of the weight of the anionic to the zwitterionic surfactant(s) in the composition can range from 1:0 to 0:1. Typical ranges are anionic:zwitterionic 4:1 to 1:4.

As used herein, "zwitterionic surfactant" refers to an amphiphilic molecule comprising a hydrophobic group and one or more hydrophilic groups comprising two moieties of opposite formal charges, or capable of bearing opposite formal charges (as a function of acid-base properties and solution pH). Sometimes such surfactants are also referred to as "amphoteric surfactants".

Suitable zwitterionic surfactants include, but are not limited to, surfactants described by formulas:

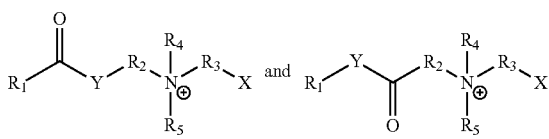

where $R_1$ is a linear, branched, saturated or unsaturated C5 to C21 hydrophobe;

$R_2$ is a linear, branched, or cyclic alkyl, hydroxyalkyl, or aromatic group;

$R_3$ is a linear or branched alkyl, hydroxyalkyl, or aromatic group;

$R_4$ is a linear or branched alkyl, hydroxyalkyl, or aromatic group;

$R_5$ is a linear or branched alkyl, hydroxyalkyl, or aromatic group; and any of $R_2$, $R_4$, or $R_5$ can by linked in a cyclic structure; and Y is —N(H)—, —N(R3)-, —O—, —S—; and X is —CO2-, —SO3-, or —SO4- or phosphate or phosphonate.

Examples of zwitterionic surfactants include:

Alkylamidoalkyl betaines of the formula:

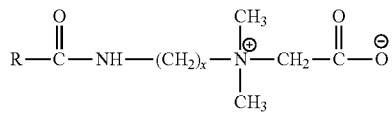

where RCO=$C_6$-$C_{24}$ acyl (saturated or unsaturated) or mixtures thereof and x=1-4. Examples include cocamidoethyl betaine (RCO=coco acyl, x=2), cocamidopropyl betaine (RCO=coco acyl, x=3), lauramidopropyl betaine (RCO=lauroyl, and x=3), myristamidopropyl betaine (RCO=myristoyl, and x=3), soyamidopropyl betaine (R=soy acyl, x=3), and oleamidopropyl betaine (RCO=oleoyl, and x=3).

Alkylamidoalkyl hydroxysultaines of the formula:

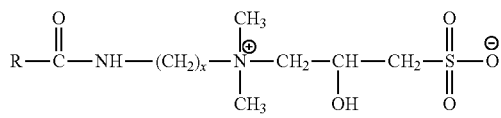

where RCO=$C_6$-$C_{24}$ acyl (saturated or unsaturated) or mixtures thereof. Examples include cocamidopropyl hydroxysultaine (RCO=coco acyl, x=3), lauramidopropyl hydroxysultaine (RCO=lauroyl, and x=3), myristamidopropyl hydroxysultaine (RCO=myristoyl, and x=3), and oleamidopropyl hydroxysultaine (RCO=oleoyl, and x=3).

Alkylamidoalkyl sultaines of the formula:

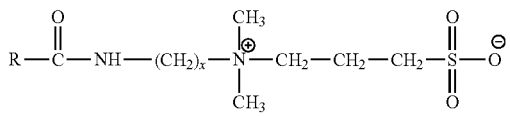

where RCO=$C_6$-$C_{24}$ acyl (saturated or unsaturated) or mixtures thereof. Examples include cocamidopropyl sultaine (RCO=coco acyl, x=3), lauramidopropyl sultaine (RCO=lauroyl, and x=3), myristamidopropyl sultaine (RCO=myristoyl, and x=3), soyamidopropyl betaine (RCO=soy acyl, x=3), and oleamidopropyl betaine (RCO=oleoyl, and x=3).

Amphoacetates of the formula:

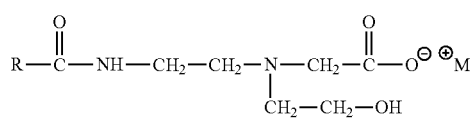

where RCO=$C_6$-$C_{24}$ acyl (saturated or unsaturated) or mixtures thereof and $M^+$=monovalent cation. Examples include sodium lauroamphoacetate (RCO=lauroyl and $M^+$=$Na^+$) and sodium cocoamphoacetate (RCO=coco acyl and $M^+$=$Na^+$).

Amphodiacetates of the formula:

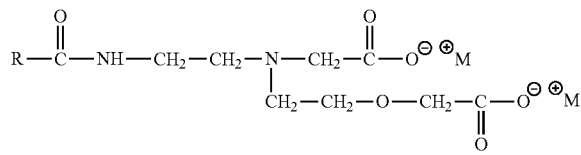

where RCO=$C_6$-$C_{24}$ acyl (saturated or unsaturated) or mixtures thereof and $M^+$=monovalent cation. Examples include disodium lauroamphodiacetate (RCO=lauroyl and M=$Na^+$) and disodium cocoamphodiacetate (RCO=coco acyl and M=$Na^+$).

Amphopropionates of the formula:

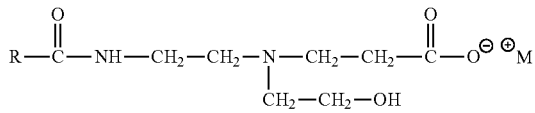

where RCO=$C_6$-$C_{24}$ acyl (saturated or unsaturated) or mixtures thereof and $M^+$=monovalent cation. Examples include sodium lauroamphopropionate (RCO=lauroyl and $M^+$=$Na^+$) and sodium cocoamphopropionate (RCO=coco acyl and $M^+$=$Na^+$).

Amphodipropionates of the formula:

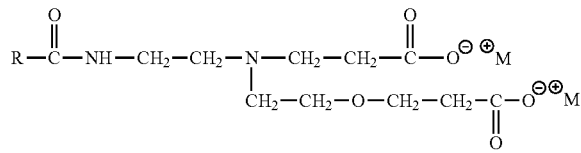

where RCO=$C_6$-$C_{24}$ acyl (saturated or unsaturated) or mixtures thereof and $M^+$=monovalent cation. Examples include disodium lauroamphodipropionate (RCO=lauroyl and $M^+$=$Na^+$) and disodium cocoamphodipropionate (RCO=coco acyl and $M^+$=$Na^+$).

Amphohydroxypropylsulfonates of the formula:

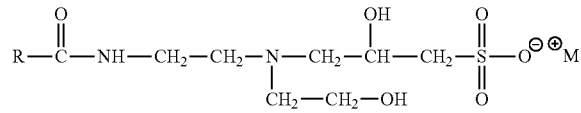

where RCO=$C_6$-$C_{24}$ acyl (saturated or unsaturated) or mixtures thereof and $M^+$=monovalent cation, such as sodium lauroamphohydroxypropylsulfonate (RCO=lauroyl and $M^+$=$Na^+$) and sodium cocoamphohydroxypropylsulfonate (RCO=coco acyl and $M^+$=$Na^+$).

Other examples include amphohydroxyalkylphosphates and alkylamidoalkyl amine oxides.

In certain embodiments of the present invention, the composition may comprise a nonionic surfactant. Suitable concentrations of nonionic surfactant are from about 0 wt % to about 15 wt %, typically from about 1-10 wt %, more typically from about 2 wt % to about 6 wt %. As used herein, the term "nonionic surfactant" refers to a surfactant molecule bearing no electrostatic charge. Any of a variety of nonionic surfactants is suitable for use in the present invention. Examples of suitable nonionic surfactants include, but are not limited to, fatty alcohol, acid, or amide ethoxylates, monoglyceride ethoxylates, sorbitan ester ethoxylates, alkyl polyglucosides, mixtures thereof, and the like. Certain preferred nonionic surfactants include polyethyleneoxy derivatives of polyol esters, wherein the polyethyleneoxy derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 ethyleneoxy units; and (3) has an average of about 1 to about 3 fatty acid residues per mole of polyethyleneoxy derivative of polyol ester. Examples of such preferred polyethyleneoxy derivatives of polyol esters include, but are not limited to PEG-80 sorbitan laurate and Polysorbate 20. PEG-80 Sorbitan Laurate is a sorbitan monoester of lauric acid ethoxylated with an average of about 80 moles of ethylene oxide. Polysorbate 20 is the laurate monoester of a mixture of sorbitol and sorbitol anhydrides condensed with approximately 20 moles of ethylene oxide.

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. Preferred alkyl glucosides comprise from about 1 to about 6 glucose residues per molecule of alkyl glucoside. A preferred glucoside is Decyl Glucoside, which is the condensation product of decyl alcohol with a glucose oligomer.

Another class of suitable nonionic surfactants is polyglycerol nonionic surfactants. Examples of polyglycerol nonionic surfactants include, but are not limited to, polyglycerol esters (PGEs), such as Polyglycerol-10 Laurate.

As used herein, the term "polyglyceryl nonionic surfactant" means an amphiphilic molecule comprising one or more nonionic hydrophilic segments comprised of a polyglyceryl moiety and one or more hydrophobic moieties. Examples of polyglyceryl nonionic surfactants include, but are not limited to, polyglyceryl esters (PGEs), such as polyglyceryl-10 laurate where PG=polyglyceryl moiety comprising ten (10) glyceryl repeat units, and R=$C_{11}H_{23}$:

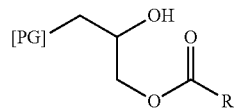

as well as, polyglyceryl-10 caprylate/caprate, polyglyceryl-10 cocoate, polyglyceryl-10 myristate, polyglyceryl-10 palmitate, polyglyceryl-10 oleate, polyglyceryl-12 laurate, and the like. PGEs of the present invention may include polyglyceryl moieties bearing multiple ester substitutions (i.e. the PGEs may be monoesters, diesters, triesters, etc.). Other polyglyceryl nonionic surfactants include polyglyceryl ethers, such as polyglyceryl-10 lauryl ether, where PG=polyglyceryl moiety comprising 10 glyceryl repeat units, and R=$C_{12}H_{25}$:

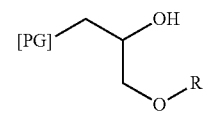

and the like. Still other polyglyceryl nonionic surfactants include polyglyceryl sorbitan fatty acid esters, such as polyglyceryl-20 sorbitan laurate, where PG=polyglycerol, the sum of all PG RUs=20, and R=$C_{11}H_{23}$. (see Bevinakatti, et al. WO 2009016375, assigned to Croda International PLC)

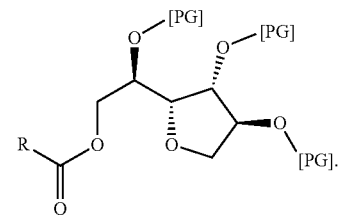

Another class of suitable nonionic surfactants includes alkanolamides, like cocamide MEA and cocamide DEA.

In certain embodiments of the present invention, the composition may further comprise an inorganic salt. Inorganic salts that are suitable for use in this invention include, but are not limited to, sodium chloride, potassium chloride, sodium bromide, potassium bromide, ammonium chloride, ammonium bromide and other mono-valent as well as multi-valent ion containing salts. Typically, compositions of the present invention will comprise from about 0.05 wt % to about 6 wt % of inorganic salt, or from about 0.1 wt % to about 4 wt % of inorganic salt, or from about 0.1 wt % to about 2 wt % of inorganic salt, or from about 0.1 wt % to about 1.5 wt % of inorganic salt.

In certain embodiments of the present invention, the composition may further comprise a cationic surfactant. Classes of cationic surfactants that are suitable for use in this invention include, but are not limited to, alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred.

The composition of this invention may further contain any other ingredients or additives typically used in personal care products, e.g. dermatological or in cosmetic formulations, including active ingredients. Examples of further ingredients or additives are surfactants, emulsifiers, viscosity controlling agents, lubricants, chelating agents, fillers, binding agents, anti-oxidants, preservatives and preservative boosters, dyes, buffering agents, pH adjusters, solvents, and benefit agents such as active ingredients, fragrances, exfoliates, emollients, moisturizers, humectants, pigments and opacifying agents, and the like, provided that they are physically and chemically compatible with the other components of the composition. Active ingredients may include, without limitation, anti-inflammatory agents, anti-bacterials, anti-fungals, anti-itching agents, moisturizing agents, plant extracts, vitamins, and the like. Also included are sunscreen actives which may be inorganic or organic in nature.

The composition of this invention may further contain thickeners, suspending agents, and rheology modifiers, which are not part of the "Polyelectrolyte Conditioning System". Examples include, but are not limited to, a) naturally-derived polysaccharides including *Cyamopsis tetragonoloba* (guar) gum, *cassia* gum, microcrystalline cellulose, ethoxylated and nonethoxylated derivatives of cellulose (e.g., hydroxyethyl and hydroxypropyl methylcellulose, etc.), and hydroxypropyl guar, b) synthetic polymers including acrylate polymers such as surfactant responsive microgels (as described e.g. in U.S. Pat. No. 9,096,755 B2, examples include Acrylates/Beheneth-25 Methacrylate/HEMA Crosspolymer and Acrylates/Beheneth-25 Methacrylate/HEMA Crosspolymer-2) and Acrylates/Aminoacrylates/C10-30 Alkyl PEG-20 Itaconate Copolymer, c) micellar thickeners, such as cocamide MIPA, lauryl lactyl lactate, or sorbitan sesquicaprylate, or polyethylene glycol-based thickeners such as PEG-150 Distearate and PEG-120 Methyl Glucose Dioleate and Trioleate, and d) other thickeners like silicones, waxes, clays, silicas, salts, natural and synthetic esters, or fatty alcohols, and e) combinations of two or more thereof and the like.

Examples of preservatives and preservative boosters include but are not limited to organic acids (like e.g., benzoic acid, lactic acid, salicylic acid), benzyl alcohol, caprylyl glycol, decylene glycol, ethylhexylglycerin, gluconolactone, methylisothazolinone, and combinations of two or more thereof, and the like.

The composition of the present invention may include dispersed insoluble particles. The dispersed particles may be benefit agents, such as oil droplets, zinc pyrithione particles, mica particles, colloidal oatmeal, and crushed walnut shells. In the compositions of the present invention, it is preferable to incorporate at least 0.025 wt % of the dispersed particles, more preferably at least 0.05 wt %, still more preferably at least 0.1 wt %, even more preferably at least 0.25 wt %, and yet more preferably at least 0.5 wt % of the dispersed particles. In the compositions of the present invention, it is preferable to incorporate no more than about 30 wt % of the dispersed particles, more preferably no more than about 15 wt %, and even more preferably no more than 10 wt %.

The pH of compositions of the present invention is adjusted to preferably from about 3 to about 7, more preferably from about 3 to about 6.5, more preferably from about 3 to about 6, more preferably from about 3 to about 5.5, more preferably from about 3 to about 5, and most preferably from about 3 to about 4.5. The pH of the composition may be adjusted as low as 3 provided that formula stability and performance (e.g., foaming, mildness and viscosity) are not negatively affected. The pH of the composition may be adjusted to the appropriate acidic value using any cosmetically acceptable organic or inorganic acid, such as citric acid, acetic acid, glycolic acid, lactic acid, malic acid, tartaric acid, hydrochloric acid, combinations of two or more thereof or the like.

EXAMPLES

The following examples are meant to illustrate the present invention, not to limit it thereto.
Test methods used in the Examples are described as follows:
Dry Precipitate Mass Yield Test:

Measurements of coacervate precipitation in diluted cleansing compositions were made using the following procedure. First, 2.5 g of cleansing composition were added to a 20 mL glass scintillation vial containing 7.5 g of DI water. The vial was closed, and mixed on a VWR Analog vortex mixer for 20 seconds. Immediately after mixing, 1 mL of the bulk dilute solution was pipetted into a 1.5 mL microcentrifuge tube and preweighed on a Mettler Toledo XS105 Analytical Balance. After the mass of the centrifuge tube with 1 mL of solution was measured, the tube was centrifuged in a VWR Galaxy Micro-centrifuge at 13,000 rpm. After centrifugation, if a visible precipitate was observed, the supernatant was removed via pipette, leaving only the polyelectrolyte-rich precipitate. The centrifuge tube was then placed in a 50° C. oven overnight, with the cap open, to remove water from the precipitate. The centrifuge tube was then reweighed with only the dry precipitate. The mass of total dilute solution and dry precipitate was then calculated by subtracting out the centrifuge tube mass from respective measurements of the centrifuge tube with 1 mL of dilution solution and dry precipitate.

The Dry Precipitate Mass Yield was calculated as the ratio of dry precipitate mass to the total mass of cationic and anionic polyelectrolytes contained in the dilute solution added to the microcentrifuge tube. In some cases, rather than a solid/viscous precipitate appearing at the bottom of the tube, a single phase was observed. These samples were denoted as exhibiting a single phase upon dilution/centrifugation, and the Dry Precipitate Mass Yield is recorded as 0.
Viscosity Tests and Significant Viscosity Change Criteria:

Determinations of apparent viscosity of the cleansing compositions were conducted on a controlled-stress rheometer (AR-2000, TA Instruments Ltd., New Castle, Del., USA). Steady-state shear rate sweeps were performed at 25.0±0.1° C. using a cone-plate geometry (50 mm diameter, 1° cone angle). Data acquisition and analysis were performed with the Rheology Advantage software v5.7.0 (TA Instruments Ltd., New Castle, Del., USA). Mid-shear viscosities are taken from steady-state flow measurements at a shear rate of 10 s$^{-1}$, and are given in centiPoise (cps). Low-shear viscosities are taken from steady-state flow measurements at a shear rate of 1 s$^{-1}$, and are given in centiPoise (cps).

As used herein, a minimum significant-change-threshold is defined as $\Delta\eta_{min}=82.65\times\eta^{0.396}$, where $\eta$ is the viscosity measured using the protocol described above. This relationship between detectable viscosity differences is consistent with qualitative observations, values from the literature, and general predictions for power-law relationships between physical values and perceived magnitudes (Bergmann Tiest, W. M., *Vision Research,* 109, 2015, 178-184, Bergmann Tiest et al., *IEEE Transactions on Haptics,* 6, 2013, 24-34, Stevens, J. C. & Guirao, M., *Science,* 144, 1964, 1157-1158). Then, in cases where a polyelectrolyte is added to a composition with viscosity $\eta_0$, we define the minimum viscosity necessary to claim an observable/noticeable change in viscosity as $\eta_{min}=\Delta\eta_{min}+\eta_0=82.65\times\eta_0^{0.396}+\eta_0$.
Yield Stress Test:

As used herein, the term "yield stress" indicates that a viscoelastic material/sample possesses solid-dominated behavior. In other words, the elastic modulus must be higher than the viscous modulus in the low strain/stress plateau region of the amplitude sweep. The yield stress value is then taken as the stress at the crossover of the storage modulus G' and the loss modulus G" (G'=G") and expressed in Pascal (Pa).

The cleansing compositions of the present invention exhibit substantially no yield stress value associated with or attributable to the Polyelectrolyte Conditioning System. That is, the compositions do not contain anionic polyelectrolytes in the Polyelectrolyte Conditioning System in an amount sufficient to provide the composition with measurable yield stress or increase in yield stress value, as determined by the method described herein. A measurable increase in yield stress value is typically about 0.01 Pa or more, or even more typically about 0.05 Pa or more, or even more typically about 0.1 Pa or more.

Determinations of the yield stress value of the cleansing compositions were conducted on a controlled-stress rheometer (AR-2000, TA Instruments Ltd., New Castle, Del., USA). Oscillatory strain amplitude sweeps from 0.1%-1000% were performed at 25.0±0.1° C. using a cone-plate geometry (50 mm diameter, 1° cone angle) at an oscillation frequency of 1 rad/s. Data acquisition and analysis were performed with the Rheology Advantage software v5.7.0 (TA Instruments Ltd., New Castle, Del., USA). The yield stress value is taken as the oscillatory stress below which the storage modulus G' exceeds the loss modulus G", and above which G" exceeds G'. In cases where G' does not exceed G" at any oscillatory stress above the sensitivity of the instrument, the yield stress value is denoted as 0 Pa. Except otherwise stated, yield stress values are given in Pascal (Pa).

Ellipsometry-Based Polyelectrolyte Deposition Test:

Evaluations of polyelectrolyte deposition efficacy of Comparative and Inventive Examples during cleansing were conducted on a model surface and measured using ellipsometry. First, 2.5 g of cleansing composition were added to a 20 mL glass scintillation vial containing 7.5 g of DI water heated to 40° C. The vial was closed, and stirred on a VWR Analog vortex mixer for 20 seconds. Immediately after stirring, 100 µL of the dilute solution were pipetted onto a 2 cm×2 cm cut chip of test-grade silicon wafer (University Wafer) (previously cleaned with deionized (DI) water and ethanol and dried), spread over the surface, and allowed to sit for 30 seconds. After tipping the silicon wafer at ~45°, 5 mL of DI water at 40° C. was dripped over the silicon chip, rinsing the dilute cleansing solution from the surface. The chip was then gently dabbed with a wipe and allowed to dry for 3-4 minutes.

The thickness of deposit on the silicon wafer was measured on an alpha-SE Spectroscopic Ellipsometer (J. A. Woolam Co., Inc) at 5 different locations on each chip before and after treatment with the cleansing solution. The layer thickness is calculated by applying a standard fit to the raw ellipsometeric data for a transparent film on a silicon substrate, using the CompleteEASE® software package. The final average deposited layer thickness is then calculated by subtracting the average layer thickness measured before applying the dilute composition from the average layer thickness measured after applying the dilute composition.

Dimethicone Deposition Test:

Evaluations of silicone deposition efficacy on skin from Inventive and Comparative Examples were conducted on a human volunteer's forearm and measured using attenuated total reflectance fourier transform infrared spectroscopy (ATR-FTIR), similar to previous evaluations performed for silicone on human skin (Klimisch, H. M. & G. Chandra, *J. Soc. Cosmet. Chem.*, 37, 1986, 73-87). ATR-FTIR measurements were taken using a REMSPEC IR TissueView™ ATR FTIR spectrometer. Acquired spectra were taken over a wave number range of 900 $cm^{-1}$ to 3500 $cm^{-1}$ at 2 $cm^{-1}$ intervals.

Dimethicone-containing formulations of Inventive and Comparative Examples were made by incorporating a sufficient quantity of a pre-emulsified dimethicone which has a dimethicone droplet size of about 0.65 µm to a formulation to obtain 5 wt % active dimethicone in the finished formulation. For example, 0.78 g of Xiameter MEM-1352 (64 wt % active dimethicone) was added to 9.22 g of formulation, for a total of 0.5 g dimethicone in 10.0 g of formulation.

The volar forearm of the subject was first washed with a cleansing composition comprised of Sodium Laureth Sulfate (SLES, 5 wt % active), Cocamidopropyl Betaine (CAPB, 5 wt % active), NaCl and Sodium Benzoate, adjusted to pH of 4.5, and thoroughly rinsed and dried with a sterile wipe. A 5 cm×7 cm rectangular area was then marked on the volar forearm. An ATR-FTIR spectrum was then acquired at the center of the marked area. Then, 100 µL of dimethicone-containing formulation and 100 µL of DI water were applied to the marked area of the forearm, and gently rubbed over the area with a gloved index finger and forefinger for 30 seconds. After the formulation was allowed to sit on the arm for an additional 30 seconds, the forearm was placed 6 inches under a stream (flow rate of 3 liters per minute) of 37° C. water from a spray faucet (with the center of the spray centered at the centered of the marked area) for 10 seconds. After rinsing, the arm was shaken briefly, the arm outside the marked area was dried with a sterile wipe, and the marked area was allowed to air dry (5-10 minutes). After drying, an ATR-FTIR spectrum from 900 $cm^{-1}$ to 3500 $cm^{-1}$ was then acquired at the center of the marked area.

For each acquired ATR-FTIR absorbance spectrum, after respective baselines are subtracted for the silicone (Si) peak (1240-1280 $cm^{-1}$) and the Amide II peak (1487-1780 cm-1), the absorbance values of the silicone peak (1240-1280 $cm^{-1}$) were normalized by the total area under the Amide II peak (sum of absorbance values from 1487-1780 $cm^{-1}$). Then, Si peak absorbance values before washing with the silicone-containing test formulation were subtracted from Si peak absorbance values after washing with the silicone-containing test formulation. The Si peak absorbance value at 1260 $cm^{-1}$ is then used as a measure of relative dimethicone deposition, as it has been used in previous work as a measure of dimethicone concentration on the skin (Klimisch, H. M. & G. Chandra, *J. Soc. Cosmet. Chem.*, 37, 1986, 73-87).

Preparation of Inventive Examples and Comparative Examples

Inventive Examples and Comparative Examples were prepared utilizing different types of formulation ingredients (i.e. raw materials from various suppliers). These materials, along with INCI/material names, abbreviations, trade names and suppliers are listed below:

Anionic Surfactants:
  Sodium Laureth Sulfate (SLES) was obtained from BASF as Texapon® N70.
  Sodium $C_{14}$-$C_{16}$ Olefin Sulfonate was obtained from Stepan as Bio-Terge® AS-40 CG K.
  Sodium Trideceth Sulfate was obtained from Stepan as Cedepal® TD403 MFLD.

Zwitterionic/Amphoteric/Nonionic Surfactants:
  Cocamidopropyl Betaine (CAPB) was obtained from Evonik Inc. as Tego® Betain F50, unless otherwise specified as Tego® Betain L7V from Evonik.
  Coco-Betaine was obtained from Solvay as Mackam® C35

Cocamidopropyl Hydroxysultaine (CAPHS) was obtained from Solvay as Miraitane® CBS.

PEG-80 Sorbitan Laurate was obtained from Croda as Tween-28® LQ (AP).

Cationic (Quaternary) Conditioning Polyelectrolytes:
  Polyquarternium-7 (PQ-7) was obtained from Lubrizol as Merquat® 7SPR.
  Polyquarternium-10 (PQ-10) was obtained from Dow Chemical as Ucare® JR-400.
  Guar Hydroxypropyltrimonium Chloride (Cationic Guar Gum) was obtained from Solvay Inc. as Jaguar® C500.
  Polyquarternium-5 (PQ-5) was obtained from Lubrizol as Merquat® 5.
  Polyquarternium-28 (PQ-28) was obtained from Ashland as Conditioneze® NT-20.
  Polyquarternium-44 (PQ-44) was obtained from BASF as Luviquat® UltraCare AT-1.

Anionic Polyelectrolytes:
  Potassium Acrylates Copolymer was obtained from Lubrizol, Inc.
  Acrylates Copolymer was obtained from Lubrizol as Carbopol® Aqua SF-1.
  Polyacrylate-33 was obtained from Solvay as Rheomer® 33T.
  Xanthan Gum was obtained from Vanderbilt Minerals as Vanzan® NF.
  Carboxymethylcellulose (CMC) was obtained from Ashland as Aqualon® CMC 7MF.
  Sodium Polyacrylate (crosslinked) was obtained as AP 80HS from Evonik Stockhausen.

Humectants:
  Glycerin was obtained from P&G Chemicals as Moon OU Glycerin.

Chelating Agents:
  Disodium EDTA was obtained from DOW as Versene® NA.
  Tetrasodium EDTA was obtained from DOW as Versene® 100XL.

Organic Acids/Preservatives:
  Sodium Benzoate, NF, FCC was obtained from Emerald Performance Materials.
  Phenonip XB was obtained from Clariant.
  Quaternium-15 was obtained from DOW as Dowicil® 200.

Benefit Agents:
  Sodium Glycolate was obtained from Acros Organics.
  Pre-emulsified dimethicone was obtained as Xiameter® MEM-1352 from Dow Corning.

Other
  Hexylene Glycol was obtained from Penta International Crop.
  Fragrance was obtained from Firmenich as Luxury 475537 F.
  Disodium Cocoamphodiacetate was obtained from Croda as Crodateric® CDA 40-LQ-(AP).
  Deionized water (DI water, also referred to as Water in the Examples below) was obtained from a Millipore Direct-Q™ System with Progard™ 2 filter.

Unless otherwise indicated, all ingredient products as received were added in amounts such that the compositions contain resulting weight percent amounts of active material. For example, 3.5 wt % active of Cocamidopropyl Betaine (as given in Table 3a) corresponds to 9 wt % Tego® Betain F50, which has an activity of 39 wt %; 3.5 wt %/39 wt %=9 wt %.

Preparation of Inventive Examples E1-E24 and Comparative Examples C1-C24, C29-C34

Inventive Examples E1-E24 and Comparative Examples C1-C24, C29-C34 were prepared as follows: To an appropriately sized vessel equipped with a hotplate and overhead mechanical stirrer, the required amounts of DI water and anionic polyelectrolyte were added and mixed at 200-250 rpm until the mixture was homogeneous. Anionic and zwitterionic/amphoteric surfactants were then added, and mixed until the solution became homogeneous. Then, aqueous solutions of sodium hydroxide and/or citric acid were added to adjust to the desired pH value 6.4-6.6. Upon stabilization of the pH, cationic polyelectrolyte was added to the mixture. In the case of cationic polyelectrolytes already supplied as aqueous suspensions, the polyelectrolyte solution was added directly to the mixture, slowly and drop-wise. For polyelectrolytes provided as dry powders, a 9 wt % premix of the polyelectrolyte in DI water was made first, then added slowly and dropwise to the mixture. Once the mixture was homogeneous, sodium chloride and sodium benzoate was added, and again allowed to mix until homogeneous. Then, aqueous solutions of sodium hydroxide and/or citric acid in DI water were added at room temperature to adjust to the desired pH (pH 4.4-4.6, if not stated otherwise). DI water was added in q.s. to 100 wt %, and the batch was allowed to mix until uniform before being discharged to an appropriate storage vessel.

Example 1a

Precipitation Measurements of Inventive (E1-E3) and Comparative Examples (C1-C3) Incorporating an Anionic Polyelectrolyte and Cationic Polyelectrolyte at Varying Weight Ratios Comparative Examples C1-C3 and Inventive Examples E1-E3, listed in Table 1a, along with Dry Precipitate Mass Yield (as measured in accord with the Dry Precipitate Mass Yield Test as described herein), are formulations with identical quantities and types of surfactant (9 wt % SLES, 2 wt % CAPB), cationic polyelectrolyte (0.6 wt % PQ-10), salt and preservative, but varying added quantities of an anionic polyelectrolyte, specifically, Acrylates Copolymer, a well-known rheology modifier and suspending agent. As shown in Table 1a, Inventive Examples E1-E3 exhibit a measurable increase in Dry Precipitate Mass Yield compared to the Comparative Example C1 containing no anionic polyelectrolyte. On the other hand, Comparative Examples C2-C3, which have anionic to cationic polyelectrolyte weight ratios greater than 1.2 (specifically, 1.67 and 2.5, respectively), exhibit no improvement in Dry Precipitate Mass Yield compared to C1.

TABLE 1a

| Material | Material class | wt % active material | | | | | |
|---|---|---|---|---|---|---|---|
| | | C1 | E1 | E2 | E3 | C2 | C3 |
| Acrylates Copolymer | Anionic polyelectrolyte | 0 | 0.1 | 0.3 | 0.6 | 1 | 1.5 |
| Polyquaternium-10 | Cationic polyelectrolyte | 0.6 | 0.6 | 0.6 | 0.6 | 0.6 | 0.6 |
| Sodium Laureth Sulfate | Anionic surfactant | 9 | 9 | 9 | 9 | 9 | 9 |
| Cocamidopropyl Betaine | Amphoteric/zwitterionic surfactant | 2 | 2 | 2 | 2 | 2 | 2 |
| Sodium Chloride | Salt | 0.4 | 0.4 | 0.4 | 0.4 | 0.4 | 0.4 |
| Sodium Benzoate | Preservative | 0.5 | 0.5 | 0.5 | 0.5 | 0.5 | 0.5 |
| Citric Acid | pH adjuster | q.s. | q.s. | q.s. | q.s. | q.s. | q.s. |
| Sodium Hydroxide | pH adjuster | q.s. | q.s. | q.s. | q.s. | q.s. | q.s. |
| Water | Vehicle | q.s. to 100 wt % | q.s. to 100 wt % | q.s. to 100 wt % | q.s. to 100 wt % | q.s. to 100 wt % | q.s. to 100 wt % |
| Anionic polyelectrolyte/cationic polyelectrolyte active weight ratio | | 0.00 | 0.17 | 0.50 | 1.00 | 1.67 | 2.50 |
| Dry Precipitate Mass Yield | | 0 | 1.47 | 2.85 | 2.24 | 0 | 0 |

Example 1b

Precipitation Measurements of Inventive (E4-E6) and Comparative Examples (C4-C6) Incorporating an Anionic Polyelectrolyte and Cationic Polyelectrolyte at Varying Weight Ratios.

Comparative Examples C4-C6 and Inventive Examples E4-E6, listed in Table 1b, along with Dry Precipitate Mass Yield (as measured in accord with the Dry Precipitate Mass Yield Test as described herein), are formulations which contain the same components, but at different levels and ratios, notably, a lower concentration of cationic polyelectrolyte PQ-10 (0.2 wt %). As shown in Table 1b, Inventive Examples E4-E6 exhibit a measurable increase in Dry Precipitate Mass Yield compared to the Comparative Example C4 containing no anionic polyelectrolyte. On the other hand, Comparative Examples C5-C6, which have an anionic to cationic polyelectrolyte weight ratios greater than 1.2 (specifically, 1.5 and 2.5, respectively), exhibit no improvement in Dry Precipitate Mass Yield compared to C4.

Example 2a

Precipitation Measurements of Inventive (E7) and Comparative Example (C7 and C8) Using a Synthetic Cationic Polyelectrolyte (PQ-7)

Comparative Examples C7-C8 and Inventive Example E7, listed in Table 2a, along with Dry Precipitate Mass Yield (as measured in accord with the Dry Precipitate Mass Yield Test as described herein), are formulations with identical quantities and types of surfactant (9 wt % SLES, 2 wt % CAPB), cationic polyelectrolyte (0.6 wt % PQ-7), salt and preservative, but varying added quantities of an anionic polyelectrolyte, specifically, Acrylates Copolymer. These compositions vary from those given in Table 1a only by the type of cationic polyelectrolyte used (the synthetic PQ-7, rather than the naturally-derived, cellulose-based PQ-10). As shown in Table 2a, Inventive Example E7 exhibits a measurable increase in Dry Precipitate Mass Yield compared to the Comparative Example C7 containing no anionic polyelectrolyte. Comparative Example C8, which has an anionic to cationic polyelectrolyte weight ratios greater than TABLE 1b

| Material | Material class | wt % active material | | | | | |
|---|---|---|---|---|---|---|---|
| | | C4 | E4 | E5 | E6 | C5 | C6 |
| Acylates Copolymer | Anionic polyelectrolyte | 0 | 0.03 | 0.1 | 0.2 | 0.3 | 0.5 |
| Polyquaternium-10 | Cationic polyelectrolyte | 0.2 | 0.2 | 0.2 | 0.2 | 0.2 | 0.2 |
| Sodium Laureth Sulfate | Anionic surfactant | 3.5 | 3.5 | 3.5 | 3.5 | 3.5 | 3.5 |
| Cocamidopropyl Betaine | Amphoteric/zwitterionic surfactant | 3.5 | 3.5 | 3.5 | 3.5 | 3.5 | 3.5 |
| Sodium Chloride | Salt | 0.4 | 0.4 | 0.4 | 0.4 | 0.4 | 0.4 |
| Sodium Benzoate | Preservative | 0.5 | 0.5 | 0.5 | 0.5 | 0.5 | 0.5 |
| Citric Acid | pH adjuster | q.s. | q.s. | q.s. | q.s. | q.s. | q.s. |
| Sodium Hydroxide | pH adjuster | q.s. | q.s. | q.s. | q.s. | q.s. | q.s. |
| Water | Vehicle | q.s. to 100 wt % | q.s. to 100 wt % | q.s. to 100 wt % | q.s. to 100 wt % | q.s. to 100 wt % | q.s. to 100 wt % |
| Anionic polyelectrolyte/cationic polyelectrolyte active weight ratio | | 0.00 | 0.15 | 0.50 | 1.00 | 1.50 | 2.50 |
| Dry Precipitate Mass Yield | | 1.86 | 2.43 | 3.34 | 2.19 | 1.57 | 1.18 |

1.2 (specifically, 2.5), exhibits no measurable increase in Dry Precipitate Mass Yield compared to the Comparative Example C7 containing no anionic polyelectrolyte.

TABLE 2a

| Material | Material class | wt % active material | | |
|---|---|---|---|---|
| | | C7 | E7 | C8 |
| Acrylates Copolymer | Anionic polyelectrolyte | 0 | 0.1 | 1.5 |
| Polyquaternium-7 | Cationic polyelectrolyte | 0.6 | 0.6 | 0.6 |
| Sodium Laureth Sulfate | Anionic surfactant | 9 | 9 | 9 |
| Cocamidopropyl Betaine | Amphoteric/ zwitterionic surfactant | 2 | 2 | 2 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0 | 1.08 | 0 |

Examples 3a-b

Precipitation Measurements of Inventive (E8-E9) and Comparative Examples (C9-C12) with Varying Surfactant Concentrations, Ratios and Chemistries Comparative Examples C9-C12 and Inventive Examples E8-E9, listed in Table 3a-3b, along with Dry Precipitate Mass Yield (as measured in accord with the Dry Precipitate Mass Yield Test as described herein), are formulations which replicate select cationic polyelectrolyte, anionic polyelectrolyte, salt and preservative levels from Table 1a and 2a, but use a lower total concentration of surfactant (7 wt % total), and a different weight ratio of anionic to zwitterionic surfactant (1:1 SLES:CAPB). As shown in Tables 3a and 3b, Inventive Examples E8 and E9, which have anionic to cationic polyelectrolyte weight ratios of 0.17, exhibit measurable increases in Dry Precipitate Mass Yield compared to their corresponding Comparative Examples containing no anionic polyelectrolyte, C9 and C11, respectively. Comparative Examples C10 and C12, which have an anionic to cationic polyelectrolyte weight ratio of 2.5, exhibit no measurable increases in Dry Precipitate Mass Yield compared to their corresponding Comparative Examples containing no anionic polyelectrolyte, C9 and C11, respectively.

TABLE 3a

| Material | Material class | wt % active material | | |
|---|---|---|---|---|
| | | C9 | E8 | C10 |
| Acrylates Copolymer | Anionic polyelectrolyte | 0 | 0.1 | 1.5 |
| Polyquaternium-10 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/ zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 2.7 | 3.11 | 0 |

TABLE 3b

| Material | Material class | wt % active material | | |
|---|---|---|---|---|
| | | C11 | E9 | C12 |
| Acrylates Copolymer | Anionic polyelectrolyte | 0 | 0.1 | 1.5 |
| Polyquaternium-7 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/ zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0.37 | 1.59 | 0 |

Example 3c

Precipitation Measurements of Inventive (E10) and Comparative Examples (C13-C14) with Varying Surfactant Concentrations, Ratios and Chemistries Comparative Examples C13-C14 and Inventive Example E10, listed in Table 3c, along with Dry Precipitate Mass Yield (as measured in accord with the Dry Precipitate Mass Yield Test as described herein), are formulations which replicate select cationic polyelectrolyte, anionic polyelectrolyte, salt and preservative levels from Table 1a and 2a, but use different chemistries of anionic surfactant (Sodium C14-C16 Olefin Sulfonate instead of SLES) and amphoteric/ zwitterionic surfactant (CAPHS instead of CAPB). As shown in Table 3c, Inventive Example E10 exhibits a measurable increase in Dry Precipitate Mass Yield compared to its corresponding Comparative Examples containing no anionic polyelectrolyte, C13. Comparative Example C14, which has an anionic to cationic polyelectrolyte weight ratio of 2.5, exhibits no measurable increases in Dry Precipitate Mass Yield compared to its corresponding Comparative Examples containing no anionic polyelectrolyte, C13.

TABLE 3c

| Material | Material class | wt % active material | | |
|---|---|---|---|---|
| | | C13 | E10 | C14 |
| Acylates Copolymer | Anionic polyelectrolyte | 0 | 0.1 | 1.5 |

TABLE 3c-continued

| Material | Material class | wt % active material | | |
|---|---|---|---|---|
| | | C13 | E10 | C14 |
| Polyquaternium-7 | Cationic polyelectrolyte | 0.6 | 0.6 | 0.6 |
| Sodium $C_{14}$-$C_{16}$ Olefin Sulfonate | Anionic surfactant | 9 | 9 | 9 |
| Cocamidopropyl Hydroxysultaine | Amphoteric/ zwitterionic surfactant | 2 | 2 | 2 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0 | 1.17 | 0 |

Examples 4a Through 4d

Measurement of Inventive (E11-E14) and Comparative (C15-C22) Examples Using a Variety of Synthetic and Naturally-Derived Cationic Polyelectrolyte Comparative Examples C15-C22 and Inventive Examples E11-E14, listed in Table 4a-4d, along with Dry Precipitate Mass Yield (as measured in accord with the Dry Precipitate Mass Yield Test as described herein), are formulations which replicate select anionic polyelectrolyte, salt and preservative levels from Table 3a, but use different chemistries of cationic polyelectrolyte (at 0.6 wt % active), specifically, Guar Hydroxypropyltrimonium Chloride, PQ-5, PQ-22, and PQ-44. As shown in Tables 4a-d, Inventive Examples E11-E14 exhibit a measurable increases in Dry Precipitate Mass Yield compared to their corresponding Comparative Examples containing no anionic polyelectrolyte, C15, C17, C19 and C21, respectively. Comparative Examples C16, C18, C20, and C22, which have an anionic to cationic polyelectrolyte weight ratio greater than 1.2 (specifically, 2.5), exhibit no measurable increases in Dry Precipitate Mass Yield compared to their corresponding Comparative Examples containing no anionic polyelectrolyte, C15, C17, C19 and C21, respectively.

TABLE 4a

| Material | Material class | wt % active material | | |
|---|---|---|---|---|
| | | C15 | E11 | C16 |
| Acylates Copolymer | Anionic polyelectrolyte | 0 | 0.1 | 1.5 |
| Guar Hydroxypropyltrimonium Chloride | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/ zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |

TABLE 4a-continued

| Material | Material class | wt % active material | | |
|---|---|---|---|---|
| | | C15 | E11 | C16 |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 2.19 | 2.7 | 0 |

TABLE 4b

| Material | Material class | wt % active material | | |
|---|---|---|---|---|
| | | C17 | E12 | C18 |
| Acylates Copolymer | Anionic polyelectrolyte | 0 | 0.1 | 1.5 |
| Polyquaternium-5 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/ zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0 | 0.46 | 0 |

TABLE 4c

| Material | Material class | wt % active material | | |
|---|---|---|---|---|
| | | C19 | E13 | C20 |
| Acylates Copolymer | Anionic polyelectrolyte | 0 | 0.1 | 1.5 |
| Polyquaternium-28 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/ zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0 | 0.9 | 0 |

TABLE 4d

| Material | Material class | wt % active material | | |
|---|---|---|---|---|
| | | C21 | E14 | C22 |
| Acylates Copolymer | Anionic polyelectrolyte | 0 | 0.1 | 1.5 |
| Polyquaternium-44 | Cationic polyelectrolyte | 0.6 | 0.6 | 0.6 |
| Sodium Laureth Sulfate | anionic surfactant | 3.5 | 3.5 | 3.5 |

TABLE 4d-continued

| | | wt % active material | | |
|---|---|---|---|---|
| Material | Material class | C21 | E14 | C22 |
| Cocamidopropyl Betaine | Amphoteric/zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0.99 | 2.33 | 0.7 |

Example 5

Precipitation Measurements of Inventive (E15-E17) and Comparative (C7, C11, C23, C24) Examples Using a Non-Crosslinked, Low Molecular Weight Anionic Polyelectrolyte Comparative Examples C7, C11, C23 and C24 and Inventive Examples E15-E17, listed in Table 5a, along with Dry Precipitate Mass Yield (as measured in accord with the Dry Precipitate Mass Yield Test as described herein), are formulations similar to compositions from Tables 2a and 3b, incorporating PQ-7 in with different ratios of SLES and CAPB; however, in this case, the compositions incorporate an alternate anionic polyelectrolyte, specifically, Potassium Acrylates Copolymer. Unlike the Acrylates Copolymer (Carbopol® AQUA SF-1), which is crosslinked, Potassium Acrylates Copolymer is a non-crosslinked polyelectrolyte with a comparatively low molecular weight. As shown in Tables 5a and 5b, Inventive Examples E15-E17 exhibit measurable increases in Dry Precipitate Mass Yield compared to corresponding Comparative Examples containing no anionic polyelectrolyte, C11 and C7. Comparative Examples C23 and C24, which have an anionic to cationic polyelectrolyte weight ratio greater than 1.2 (specifically, 2.5), exhibits no measurable increase in Dry Precipitate Mass Yield compared to its corresponding Comparative Examples containing no anionic polyelectrolyte, C11 and C7, respectively.

TABLE 5a

| | | wt % active material | | | |
|---|---|---|---|---|---|
| Material | Material class | C11 | E15 | E16 | C23 |
| Potassium Acrylates Copolymer | Anionic polyelectrolyte | 0 | 0.1 | 0.5 | 1.5 |
| Polyquaternium-7 | Cationic polyelectrolyte | 0.6 | 0.6 | 0.6 | 0.6 |
| Sodium Laureth Sulfate | Anionic surfactant | 3.5 | 3.5 | 3.5 | 3.5 |
| Cocamidopropyl Betaine | Amphoteric/zwitterionic surfactant | 3.5 | 3.5 | 3.5 | 3.5 |
| Sodium Chloride | Salt | 0.4 | 0.4 | 0.4 | 0.4 |
| Sodium Benzoate | Preservative | 0.5 | 0.5 | 0.5 | 0.5 |
| Citric Acid | pH adjuster | q.s. | q.s. | q.s. | q.s. |
| Sodium Hydroxide | pH adjuster | q.s. | q.s. | q.s. | q.s. |
| Water | Vehicle | q.s. to 100 wt % | q.s. to 100 wt % | q.s. to 100 wt % | q.s. to 100 wt % |
| Anionic polyelectrolyte/cationic polyelectrolyte active weight ratio | | 0.00 | 0.17 | 0.83 | 2.50 |
| Dry Precipitate Mass Yield | | 0.37 | 0.63 | 0.67 | 0 |

TABLE 5b

| | | wt % active material | | |
|---|---|---|---|---|
| Material | Material class | C7 | E17 | C24 |
| Potassium Acrylates Copolymer | Anionic polyelectrolyte | 0 | 0.1 | 1.5 |
| Polyquaternium-7 | Cationic polyelectrolyte | 0.6 | 0.6 | 0.6 |
| Sodium Laureth Sulfate | Anionic surfactant | 9 | 9 | 9 |
| Cocamidopropyl Betaine | Amphoteric/zwitterionic surfactant | 2 | 2 | 2 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0 | 0.21 | 0 |

Example 6

Preparation and Precipitation Measurements of Comparative Examples (C25-C28)

Comparative Examples C25 & C26, described in Table 6a, are made to replicate Examples 10 and 11 of International Patent Application WO 2005/023969. The selection of raw materials and formulation processes replicates the materials and process referenced in this publication, given available commercial materials. These compositions were made as follows:

50 wt % of DI water was added to a beaker. If included, Acrylates Copolymer was added to the water with mixing. The PEG-80 Sorbitan Laurate was then added thereto with mixing. The following ingredients were added thereto independently with mixing until each respective resulting mixture was homogeneous: Cocamidopropylbetaine (Tego Betain L7V), Sodium Trideceth Sulfate, Glycerin, Polyquaternium-10, Quaternium-15 and Tetrasodium EDTA. The pH of the resulting solution was then adjusted with either a 20 wt % Sodium Hydroxide solution or a 20 wt %/Citric Acid solution until a final pH of about 6.3-6.6 was obtained. The remainder of the water was then added thereto.

Dry Precipitate Mass Yield was measured in accord with the Dry Precipitate Mass Yield Test as described herein. As listed in Table 6a, Comparative Example C26 has an anionic to cationic polyelectrolyte weight ratio of 1.86 and exhibits no measurable increase in Dry Precipitate Mass Yield compared to their corresponding Comparative Examples containing no anionic polyelectrolyte, C25.

TABLE 6a

| Material | wt % active material | |
|---|---|---|
| | C25 | C26 |
| Acrylates Copolymer | 0.00 | 0.26 |
| Polyquaternium-10 | 0.14 | 0.14 |
| Sodium Trideceth Sulfate | 6.00 | 6.00 |
| Cocamidopropyl Betaine | 3.40 | 3.40 |
| PEG-80 Sorbitan Laurate | 3.30 | 3.30 |
| Glycerin | 1.88 | 1.88 |
| Tetrasodium EDTA | 0.26 | 0.26 |
| Quaternium-15 | 0.05 | 0.05 |
| Sodium Hydroxide | q.s. | q.s. |
| Citric Acid | q.s. | q.s. |
| Water | q.s. to 100 wt % | q.s. to 100 wt % |
| Anionic polyelectrolyte/cationic polyelectrolyte active weight ratio | 0.00 | 1.86 |
| Dry Precipitate Mass Yield | 0 | 0 |

Comparative Examples C27 & C28, described in Table 6b, were made to model Examples 4 and 1 in U.S. Pat. No. 7,776,318, respectively. The only modification to these formulations is the exclusion of glycol distearate, an opacifier which is not solubilized in formulations and sediments out upon dilution. Such suspended solids interfere with the Dry Precipitate Mass Yield Test described herein, and are thus excluded from the following formulation to provide unobstructed insight into the polyelectrolyte precipitation properties of these compositions. The selection of raw materials and formulation processes otherwise replicates the materials and process referenced in this patent, given currently available commercial materials. These compositions were made as follows:

Water, preserving agents, glycerin and hexylene glycol were added to an appropriately sized vessel equipped with a hotplate and overhead mechanical stirrer. Once the batch was heated to 50° C., some of the sodium laureth sulfate was added until fully dissolved. Then, sequentially, Disodium EDTA, Polyquarternium-7, and Acrylates Copolymer were added, with sufficient time given between each additional ingredient to observe complete and even dispersal. The pH of the solution was then adjusted to 6.4-6.6 through addition of dilute sodium hydroxide. Fragrance was then added to the mixture.

Subsequently, Coco-Betaine, then Disodium Cocoamphodiacetate are added. Sodium Glycolate and Sodium Chloride are added after that. Finally, the pH of the solution was adjusted using dilutions of sodium hydroxide and/or citric acid to a pH of 6.4-6.6 (for Examples containing Phenonip XB as a preservative) and the remaining water was added in q.s. to 100 wt %. The batch was allowed to mix until uniform before being discharged to an appropriate storage vessel.

Dry Precipitate Mass Yield was measured in accord with the Dry Precipitate Mass Yield Test as described herein. As listed in Table 6b, the composition C28 has an anionic to cationic polyelectrolyte weight ratio of 2.36 and exhibits no measurable increase in Dry Precipitate Mass Yield compared to the corresponding Comparative Examples containing no anionic polyelectrolyte, C27.

TABLE 6b

| Material | wt % active material | |
|---|---|---|
| | C27 | C28 |
| Acrylates Copolymer | 0 | 0.26 |
| Polyquaternium-7 | 0.11 | 0.11 |
| Sodium Laureth Sulfate | 9.8 | 9.8 |
| Coco-Betaine | 1.99 | 1.99 |

TABLE 6b-continued

| Material | wt % active material | |
|---|---|---|
| | C27 | C28 |
| Disodium Cocoamphodiacetate | 0.6 | 0.6 |
| Glycerin | 1 | 1 |
| Hexylene Glycol | 1 | 1 |
| Disodium EDTA | 0.26 | 0.26 |
| Sodium Glycolate | 0.12 | 0.12 |
| Sodium Chloride | 2.16 | 2.16 |
| Fragrance | 0.25 | 0.25 |
| Preservative (Phenonip XB) | 1 | 1 |
| Sodium Hydroxide | q.s. | q.s. |
| Citric Acid | q.s. | q.s. |
| Water | q.s. to 100 wt % | q.s. to 100 wt % |
| Anionic polyelectrolyte/cationic polyelectrolyte active weight ratio | 0.00 | 2.36 |
| Dry Precipitate Mass Yield | 0 | 0 |

Examples 7a Through 7g

Precipitation Measurements of Inventive (E18-E24) and Comparative Examples (C9, C11, C29-32) Using a Variety of Anionic Polyelectrolyte Chemistries Comparative Examples C9, C11, C29-34 and Inventive Examples E18-E24, listed in Tables 7a-7g, along with Dry Precipitate Mass Yield (as measured in accord with the Dry Precipitate Mass Yield Test as described herein), are formulations which replicate select anionic polyelectrolyte, salt and preservative levels from Table 3a-3b, but use different concentrations and chemistries of anionic polyelectrolyte. As shown in Tables 7a through 7g, Inventive Examples E18-E24 exhibit a measurable increases in Dry Precipitate Mass Yield compared to their corresponding Comparative Examples containing no anionic polyelectrolyte, C9 and C11. Comparative Examples C29-34, which have an anionic to cationic polyelectrolyte weight ratio greater than 1.2 (specifically, 2.5 or 3.33), exhibit no measurable increases in Dry Precipitate Mass Yield compared to their corresponding Comparative Examples containing no anionic polyelectrolyte, C9 and C11.

TABLE 7a

| Material | Material class | wt % active material | | |
|---|---|---|---|---|
| | | C9 | E18 | C29 |
| Polyacrylate-33 | Anionic polyelectrolyte | 0 | 0.1 | 2 |
| Polyquaternium-10 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/ zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 3.33 |
| Dry Precipitate Mass Yield | | 2.7 | 3.3 | 0 |

TABLE 7b

| Material | Material class | wt % active material | | |
|---|---|---|---|---|
| | | C9 | E19 | C30 |
| Carboxymethycellulose | Anionic polyelectrolyte | 0 | 0.1 | 1.5 |
| Polyquaternium-10 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 2.7 | 3.32 | 1.11 |

TABLE 7c

| Material | Material class | wt % active material | | |
|---|---|---|---|---|
| | | C11 | E20 | C31 |
| Xanthan Gum | Anionic polyelectrolyte | 0 | 0.1 | 1.5 |
| Polyquaternium-10 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 2.7 | 3.13 | 1.23 |

TABLE 7d

| Material | Material class | wt % active material | | |
|---|---|---|---|---|
| | | C11 | E21 | C32 |
| Polyacrylate-33 | Anionic polyelectrolyte | 0 | 0.1 | 2 |
| Polyquaternium-7 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 3.33 |
| Dry Precipitate Mass Yield | | 0.37 | 1.65 | 0 |

TABLE 7e

| Material | Material class | wt % active material | | |
|---|---|---|---|---|
| | | C11 | E22 | C33 |
| Carboxymethycellulose | Anionic polyelectrolyte | 0 | 0.1 | 1.5 |
| Polyquaternium-7 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0.37 | 0.55 | 0.23 |

TABLE 7f

| Material | Material class | wt % active material | | |
|---|---|---|---|---|
| | | C11 | E23 | C34 |
| Xanthan Gum | Anionic polyelectrolyte | 0 | 0.1 | 1.5 |
| Polyquaternium-7 | Cationic polyelectrolyte | 0.6 | 0.6 | 0.6 |
| Sodium Laureth Sulfate | Anionic surfactant | 3.5 | 3.5 | 3.5 |
| Cocamidopropyl Betaine | Amphoteric/zwitterionic surfactant | 3.5 | 3.5 | 3.5 |
| Sodium Chloride | Salt | 0.4 | 0.4 | 0.4 |
| Sodium Benzoate | Preservative | 0.5 | 0.5 | 0.5 |
| Citric Acid | pH adjuster | q.s. | q.s. | q.s. |
| Sodium Hydroxide | pH adjuster | q.s. | q.s. | q.s. |
| Water | Vehicle | q.s. to 100 wt % | q.s. to 100 wt % | q.s. to 100 wt % |
| Anionic polyelectrolyte/cationic polyelectrolyte active weight ratio | | 0.00 | 0.17 | 2.50 |
| Dry Precipitate Mass Yield | | 0.37 | 0.52 | 0.10 |

TABLE 7g

| Material | Material class | wt % active material | |
|---|---|---|---|
| | | C11 | E24 |
| Sodium Polyacrylate (crosslinked) | Anionic polyelectrolyte | 0 | 0.1 |
| Polyquaternium-7 | Cationic polyelectrolyte | 0.6 | 0.6 |
| Sodium Laureth Sulfate | Anionic surfactant | 3.5 | 3.5 |
| Cocamidopropyl Betaine | Amphoteric/zwitterionic surfactant | 3.5 | 3.5 |
| Sodium Chloride | Salt | 0.4 | 0.4 |
| Sodium Benzoate | Preservative | 0.5 | 0.5 |
| Citric Acid | pH adjuster | q.s. | q.s. |
| Sodium Hydroxide | pH adjuster | q.s. | q.s. |
| Water | Vehicle | q.s. to 100 wt % | q.s. to 100 wt % |
| Anionic polyelectrolyte/cationic polyelectrolyte active weight ratio | | 0.00 | 0.17 |
| Dry Precipitate Mass Yield | | 0.37 | 0.56 |

Examples 8a Through 8e

Comparisons of Rheological Properties of Inventive (E1-E3, E7-E9, E18-E20) and Comparative Examples (C1-C3, C7-C12, C29-31)

A selection of the previously listed Comparative and Inventive Examples were tested according to the Viscosity Tests and Yield Stress Tests described herein. The rheological properties of compositions described in Table 1a are listed in Table 8a. The amount of Acrylates Copolymer included in Inventive Examples E1-E3, which demonstrate enhanced precipitation (as previously shown in Table 1a), is not sufficient to increase measured viscosity above $\eta_{min}$, the minimum value needed to denote a significant/perceptible change in viscosity compared to the system with no anionic polyelectrolyte described herein. Likewise, the inventive compositions E1-E3 exhibit no measurable yield stress value. Only in Comparative Examples C2-C3 (which do not exhibit enhanced precipitation) is there sufficient Acrylates Copolymer (1-1.5 wt %) to cause a measurable yield stress and significant increase in viscosity. Therefore, the use of the crosslinked ASE Acrylates Copolymer in Inventive Examples E1-E3 falls outside of the polyelectrolyte's prescribed use as a suspending agent, thickener, or rheology modifier.

TABLE 8a

Rheological properties for composition containing 9 wt % SLES, 2 wt % CAPB and 0.6 wt % PQ-10

| Example | Anionic polyelectrolyte concentration (active wt %) | Anionic polyelectrolyte/cationic polyelectrolyte active weight ratio | Yield stress (Pa) | $\eta_{min}$ (cps) |
|---|---|---|---|---|
| C1 | 0 | 0.00 | 0.00 | 569.02 |

Rheological properties for compositions containing 9 wt % SLES, 2 wt % CAPB, 0.6 wt % PQ-10 and Acrylates Copolymer

| Example | Acrylates Copolymer concentration (active wt %) | Anionic polyelectrolyte/cationic polyelectrolyte active weight ratio | Yield stress (Pa) | Mid-shear viscosity $\eta$ (cps) |
|---|---|---|---|---|
| E1 | 0.1 | 0.17 | 0.00 | 96.1 |
| E2 | 0.3 | 0.50 | 0.00 | 175.1 |
| E3 | 0.6 | 1.00 | 0.00 | 465.5 |
| C2 | 1 | 1.67 | 1.97 | 1515 |
| C3 | 1.5 | 2.50 | 8.66 | 4435 |

The use of Acrylates Copolymer is similarly shown to not impart measurable yield stress or significant changes in viscosity in Inventive Examples including varying surfactant blends and cationic polyelectrolyte chemistries, and shown in Tables 8b-8d.

TABLE 8b

Rheological properties for composition containing 9 wt % SLES, 2 wt % CAPB and 0.6 wt % PQ-7

| Example | Anionic polyelectrolyte concentration (active wt %) | Anionic polyelectrolyte/cationic polyelectrolyte active weight ratio | Yield stress (Pa) | $\eta_{min}$ (cps) |
|---|---|---|---|---|
| C7 | 0 | 0.00 | 0.00 | 286.68 |

Rheological properties for compositions containing 9% SLES, 2% CAPB, 0.6% PQ-7 and Acrylates Copolymer

| Example | Acrylates Copolymer concentration (active wt %) | Anionic polyelectrolyte/cationic polyelectrolyte active weight ratio | Yield stress (Pa) | Mid-shear viscosity $\eta$ (cps) |
|---|---|---|---|---|
| E7 | 0.1 | 0.17 | 0.00 | 24.06 |
| C8 | 1.5 | 2.50 | 7.05 | 3426 |

TABLE 8c

Rheological properties for composition containing 3.5 wt % SLES, 3.5 wt % CAPB and 0.6 wt % PQ-10

| Example | Anionic polyelectrolyte concentration (active wt %) | Anionic polyelectrolyte/cationic polyelectrolyte active weight ratio | Yield stress (Pa) | $\eta_{min}$ (cps) |
|---|---|---|---|---|
| C11 | 0 | 0.00 | 0.00 | 3126 |

Rheological properties for compositions containing 9 wt % SLES, 2 wt % CAPB, 0.6 wt % PQ-10 and Acrylates Copolymer

| Example | Acrylates Copolymer concentration (active wt %) | Anionic polyelectrolyte/cationic polyelectrolyte active weight ratio | Yield stress (Pa) | Mid-shear viscosity $\eta$ (cps) |
|---|---|---|---|---|
| E9 | 0.1 | 0.17 | 0.00 | 1626 |
| C12 | 1.5 | 2.50 | 8.65 | 4963 |

TABLE 8d

Rheological properties for composition containing 3.5 wt % SLES, 3.5 wt % CAPB and 0.6 wt % PQ-7

| Example | Anionic polyelectrolyte concentration (active wt %) | Anionic polyelectrolyte/cationic polyelectrolyte active weight ratio | Yield stress (Pa) | $\eta_{min}$ (cps) |
|---|---|---|---|---|
| C9 | 0 | 0.00 | 0.00 | 1406 |

Rheological properties for compositions containing 3.5 wt % SLES, 3.5 wt % CAPB, 0.6 wt % PQ-7 and Acrylates Copolymer

| Example | Acrylates Copolymer concentration (active wt %) | Anionic polyelectrolyte/cationic polyelectrolyte active weight ratio | Yield stress (Pa) | Mid-shear viscosity $\eta$ (cps) |
|---|---|---|---|---|
| E8 | 0.1 | 0.17 | 0.00 | 1347 |
| C10 | 1.5 | 2.50 | 12.52 | 4435 |

The rheological properties of Inventive Examples E18 and E19, which use alternative anionic rheology modifying polyelectrolytes (specifically, Carboxymethylcellose, Polyacrylate-33 and Xanthan Gum) are displayed in Table 8e. Again, the use of these anionic polyelectrolytes at the low levels necessary for increased polyelectrolyte precipitation does not impart a yield stress or significant changes in viscosity. Therefore, the use of these alternate anionic rheology modifiers in Inventive Examples falls outside of their prescribed use as suspending agents, thickeners, or viscosity modifiers.

TABLE 8e

Viscosity for formulation containing 3.5 wt % SLES, 3.5 wt % CAPB and 0.6 wt % PQ-10

| Example | Anionic polyelectrolyte concentration (active wt %) | Anionic polyelectrolyte/cationic polyelectrolyte active weight ratio | Yield stress (Pa) | $\eta_{min}$ (cps) |
|---|---|---|---|---|
| C11 | 0 | 0.00 | 0.00 | 3782 |

Rheological properties for compositions containing 3.5 wt % SLES, 3.5 wt % CAPB and 0.6 wt % PQ-10 and Acrylates Copolymer

| Example | Acrylates Copolymer concentration (active wt %) | Anionic polyelectrolyte/cationic polyelectrolyte active weight ratio | Yield stress (Pa) | Low-shear viscosity $\eta$ (cps) |
|---|---|---|---|---|
| E9 | 0.1 | 0.17 | 0.00 | 2065 |
| C12 | 1.5 | 2.50 | 8.66 | 12520 |

Rheological properties for compositions containing 3.5 wt % SLES, 3.5 wt % CAPB and 0.6 wt % PQ-10 and Carboxymethylcellulose

| Example | Carboxymethylcellulose concentration (active wt %) | Anionic polyelectrolyte/cationic polyelectrolyte active weight ratio | Yield stress (Pa) | Low-shear viscosity $\eta$ (cps) |
|---|---|---|---|---|
| E19 | 0.1 | 0.17 | 0.00 | 3470 |
| C30 | 1.5 | 2.50 | 0.00 | 20970 |

Rheological properties for compositions containing 3.5 wt % SLES, 3.5 wt % CAPB and 0.6 wt % PQ-10 and Polyacrylate-33

| Example | Polyacrylate-33 concentration (active wt %) | Anionic polyelectrolyte/cationic polyelectrolyte active weight ratio | Yield stress (Pa) | Low-shear viscosity $\eta$ (cps) |
|---|---|---|---|---|
| E18 | 0.1 | 0.17 | 0.00 | 2553 |
| C29 | 1.5 | 2.50 | 4.94 | 6321 |

Rheological properties for compositions containing 3.5 wt % SLES, 3.5 wt % CAPB and 0.6 wt % PQ-10 and Xanthan Gum

| Example | Xanthan Gum concentration active wt %) | Anionic polyelectrolyte/cationic polyelectrolyte active weight ratio | Yield stress (Pa) | Low-shear viscosity $\eta$ (cps) |
|---|---|---|---|---|
| E20 | 0.1 | 0.17 | 0.00 | 2743 |
| C31 | 1.5 | 2.50 | 0.00 | 27190 |

Example 9

Comparison of Cleanser Polyelectrolyte Film Deposition on an In-Vitro Substrate Between Inventive (E1) and Comparative Examples (C1, C3)

The film/polyelectrolyte deposition efficacy of a set of Comparative and Inventive Examples with comparable compositions except for concentration of anionic polyelectrolyte (C1, E1 and C3, described in Table 1a) is evaluated according to the Ellipsometry-based Polyelectrolyte Deposition Test as described herein. The results seen in Table 9 show that Inventive Examples E1 demonstrates an increase of deposited film thickness of ~40% compared to the Comparative Examples C1 and C3 (with anionic/cationic polyelectrolyte active weight ratios 0 and 2.5, respectively).

TABLE 9

| Example | PQ-10 concentration (wt % active) | Acrylates Copolymer concentration (wt % active) | Anionic/cationic polyelectrolyte active weight ratio | Average deposited film thickness (nm) |
|---|---|---|---|---|
| C1 | 0.6 | 0 | 0 | 1.10 |
| E1 | 0.6 | 0.1 | 0.17 | 1.63 |
| C3 | 0.6 | 1.5 | 2.5 | 1.25 |

Example 10

Evaluation and Comparison of Skin Feel Between Inventive Example (E9) and Comparative Example (C11)

Skin feel after washing with Comparative Example C8 and Inventive Example E6 (with comparable compositions except for concentration of anionic polyelectrolyte, described in Table 3b) and then drying were compared qualitatively by three volunteers according to a Sensory Evaluation Test. In this test, for the purpose of skin equilibration, participants first wash their hands and forearms with 1 mL of a standard surfactant solution (5 wt % active Sodium Laureth Sulfate, 5 wt % active Cocamidopropyl Betaine, pH 4.5, DI water). After thorough rinsing (60 sec at ~3 liters per minute with 35-45° C. tap water), 1 mL of a test composition (C8 or E6, respectively) was dispensed into the wet palm. Participants wash their wet hands and forearms for 30 sec by applying circular motions of the hands on the forearms. After rinsing (30 sec at ~3 liters per minute with 35-45° C. tap water), participants dabbed their hands and forearms dry with a paper towel, and let their hands and arms air-dry completely for approximately 120 sec. They then describe the sensory feel of their skin by letting fingers glide over their hands and forearms. Descriptions of the dry feel of skin after use of the Comparative and Inventive Examples are listed in Table 10. It is shown here that the addition of 0.1 wt % of Acrylates Copolymer not only significantly increases the amount of precipitate measured in the Relative Dry Precipitate Mass Yield Test (as displayed in Table 1a), but also changes the general consensus on resulting skin feel from cleansing from "soft" to "powdery" after drying. This indicates a change in the tactile properties of the deposited film.

TABLE 10

| | Example C11 | Example E9 |
|---|---|---|
| PQ-7 concentration (active wt %) | 0.6 | 0.6 |
| Acrylates Copolymer (active wt %) | 0 | 0.1 |
| Anionic polyelectrolyte/cationic polyelectrolyte active weight ratio | 0 | 0.17 |
| Comments from subjects | "soft, slippery, not powdery" | "smooth, powdery", satin-like" |

Example 11

Comparison of Dimethicone Deposition from Formulation Use on Human Skin Between Inventive (E11) and Comparative (C15) Examples The dimethicone deposition efficacy of a pair of Comparative and Inventive Examples containing 0.6 wt % Guar Hydroxypropyltrimonium Chloride, with identical compositions except for concentration of anionic polyelectrolyte, C15 (no anionic polyelectrolyte) and E11 (0.1 wt % Acrylates Copolymer) (as described in Table 4a above) were evaluated according to the Dimethicone Deposition Test as described herein. The Si peak intensity at 1260 cm$^{-1}$, which correlates to the concentration of dimethicone on human skin, is shown in Table 11. These data indicate a marked improvement in dimethicone deposition from the Comparative Example C15 to the Inventive Example E11.

TABLE 11

| Example | Anionic/cationic polyelectrolyte active weight ratio | Si peak intensity @ 1260 cm−1 (a.u.) |
|---|---|---|
| C15 | 0 | 55 |
| E11 | 0.17 | 234 |

We claim:

1. A composition, comprising, in a cosmetically acceptable aqueous medium,
   a) about 0.6 weight percent of a cationic polyelectrolyte,
   b) at least one surfactant; and
   (c) from about 0.01 to about 1.2 weight percent of an anionic polyelectrolyte, wherein the weight ratio of said anionic polyelectrolyte to said cationic polyelectrolyte is from about 0.05 to about 1.2, wherein said composition exhibits a viscosity change that is below a minimum significant-change-threshold ($\Delta\eta_{min}$) and exhibits no measurable yield stress or increase in yield stress value when compared to a substantially identical composition that does not contain from about 0.01 to about 1.2 weight percent of said anionic polyelectrolyte, at a weight ratio of anionic polyelectrolyte to cationic polyelectrolyte of from about 0.05 to about 1.2.

2. The composition of claim 1 wherein the weight ratio of said anionic polyelectrolyte to said cationic polyelectrolyte is about 0.1 to about 1.

3. The composition of claim 1 comprising from about 0.1 weight percent to about 1 weight percent of said anionic polyelectrolyte.

4. The composition of claim 1 comprising from about 1 weight percent to about 25 weight percent of said surfactant.

5. The composition of claim 1 comprising from about 3 weight percent to about 15 weight percent of said surfactant.

6. The composition of claim 1 wherein a Dry Precipitate Mass Yield upon dilution of said composition is greater than of a Dry Precipitate Mass Yield upon dilution of a substantially identical composition that does not comprise from about 0.01 weight percent to about 1.2 weight percent of said anionic polyelectrolyte, at a weight ratio of said anionic polyelectrolyte to said cationic polyelectrolyte of from about 0.05 to about 1.

7. The composition of claim 1 wherein a Dry Precipitate Mass Yield upon dilution of said composition is increased by 10% or more compared to a substantially identical composition that does not contain from about 0.01 to about 1.2 weight percent of said anionic polyelectrolyte, at a weight ratio of anionic polyelectrolyte to cationic polyelectrolyte of from about 0.05 to about 1.2.

8. The composition of claim 1 wherein a Dry Precipitate Mass Yield upon dilution of said composition is increased by 20% or more compared to a substantially identical composition that does not comprise from about 0.01 weight percent to about 1.2 weight percent of said anionic polyelectrolyte.

9. The composition of claim 1 wherein a Dry Precipitate Mass Yield upon dilution of said composition is increased by 40% or more compared to a substantially identical composition that does not comprise from about 0.01 weight percent to about 1.2 weight percent of said anionic polyelectrolyte.

10. The composition of claim 1 wherein said anionic polyelectrolyte is selected from the group consisting of polyelectrolytes derived from ethylenically unsaturated monomers containing anionic and anionically-ionizable monomers, anionic and anionically ionizable polysaccharides and polysaccharide derivatives thereof and anionic or anionically ionizable polypeptides or proteins or hybrid (co)polymers.

11. The composition of claim 1 wherein said cationic polyelectrolyte is selected from the group consisting of polyelectrolytes derived from ethylenically unsaturated monomers containing cationic protonated amine or quaternary ammonium functionalities, cationic and cationically-ionizable polysaccharides and polysaccharide derivatives thereof, and cationic or cationically-ionizable polypeptides or proteins or hybrid (co)polymers.

12. The composition of claim 1 wherein said surfactant is selected from the group consisting of anionic, zwitterionic, nonionic and cationic surfactants.

* * * * *